United States Patent
Shigeta

(10) Patent No.: US 10,022,074 B2
(45) Date of Patent: Jul. 17, 2018

(54) ENDOSCOPE SYSTEM, PROCESSOR DEVICE FOR ENDOSCOPE SYSTEM, OPERATION METHOD FOR ENDOSCOPE SYSTEM, AND OPERATION METHOD FOR PROCESSOR DEVICE

(71) Applicant: FUJIFILM Corporation, Tokyo (JP)

(72) Inventor: Norimasa Shigeta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 764 days.

(21) Appl. No.: 14/590,588

(22) Filed: Jan. 6, 2015

(65) Prior Publication Data

US 2015/0216460 A1 Aug. 6, 2015

(30) Foreign Application Priority Data

Feb. 6, 2014 (JP) .................. 2014-021779

(51) Int. Cl.
| | |
|---|---|
| *A61B 5/1455* | (2006.01) |
| *A61B 1/06* | (2006.01) |
| *A61B 5/1459* | (2006.01) |
| *A61B 5/00* | (2006.01) |
| *A61B 1/05* | (2006.01) |

(Continued)

(52) U.S. Cl.
CPC ...... *A61B 5/14552* (2013.01); *A61B 1/00009* (2013.01); *A61B 1/00045* (2013.01); *A61B 1/04* (2013.01); *A61B 1/05* (2013.01); *A61B 1/063* (2013.01); *A61B 1/0638* (2013.01); *A61B 1/0646* (2013.01); *A61B 1/0653* (2013.01); *A61B 1/0669* (2013.01); *A61B 5/1459* (2013.01); *A61B 5/7207* (2013.01); *G06T 7/0014* (2013.01); *G06T 2207/10024* (2013.01); *G06T 2207/10068* (2013.01);

(Continued)

(58) Field of Classification Search
None
See application file for complete search history.

(56) References Cited

U.S. PATENT DOCUMENTS

| | | |
|---|---|---|
| 2012/0116192 A1 | 5/2012 | Saito |
| 2012/0157775 A1 | 6/2012 | Yamaguchi |
| 2013/0113906 A1 | 5/2013 | Saito |

FOREIGN PATENT DOCUMENTS

| | | |
|---|---|---|
| JP | 2012-100800 A | 5/2012 |
| JP | 2012-130429 A | 7/2012 |
| JP | 2013-99464 A | 5/2013 |

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

An endoscope system includes: a phosphor and first and second blue laser light sources that emit first white light and second white light having different emission spectrums; a sensor that images an observation target under illumination with the first white light and outputs a first image signal and images the observation target under illumination with the second white light and outputs a second image signal; a movement amount calculation unit that calculates the movement amount of the observation target based on the first or second image signal; and an oxygen saturation calculation unit that calculates the oxygen saturation based on the movement amount in at least one of a first mode, in which the oxygen saturation is calculated using the first and second image signals, and a second mode, in which the oxygen saturation is calculated using the first image signal.

17 Claims, 21 Drawing Sheets

(51) Int. Cl.
*A61B 1/00* (2006.01)
*A61B 1/04* (2006.01)
*G06T 7/00* (2017.01)

(52) U.S. Cl.
CPC .............. *G06T 2207/10152* (2013.01); *G06T 2207/20021* (2013.01); *G06T 2207/30096* (2013.01)

ENDOSCOPE SYSTEM, PROCESSOR DEVICE FOR ENDOSCOPE SYSTEM, OPERATION METHOD FOR ENDOSCOPE SYSTEM, AND OPERATION METHOD FOR PROCESSOR DEVICE

CROSS-REFERENCE TO RELATED APPLICATIONS

The present application claims priority under 35 U.S.C. § 119 to Japanese Patent Application No. 2014-21779, filed on Feb. 6, 2014, all of which are hereby expressly incorporated by reference into the present application.

BACKGROUND OF THE INVENTION

1. Field of the Invention

The present invention relates to an endoscope system, a processor device for an endoscope system, an operation method for an endoscope system, and an operation method for a processor device for calculating biological function information regarding the oxygen saturation of blood hemoglobin from an image signal obtained by imaging an observation target in a subject.

2. Description of the Related Art

In the medical field, it is common to perform diagnosis using an endoscope system including a light source device, an endoscope, and a processor device. In recent years, diagnosis of a lesion using the oxygen saturation of blood hemoglobin in biological function information has been performed. As a method of acquiring the oxygen saturation, a method is known in which first signal light and second signal light having different waveguide bands and different light absorption coefficients for oxygenated hemoglobin and reduced hemoglobin are alternately emitted to blood vessels in the mucous membrane and reflected light beams of the first and second signal light beams are detected by a sensor located at the distal end of the endoscope (refer to JP2012-100800A, JP2012-130429A, and JP2013-099464A). The ratio between signal values (hereinafter, referred to as a signal ratio) of pixels of an image signal corresponding to the reflected light of the first signal light detected by the sensor and an image signal corresponding to the reflected light of the second signal light detected by the sensor is maintained as a fixed value if there is no change in the oxygen saturation in the blood vessel. However, if there is a change in the oxygen saturation, the signal ratio is also changed accordingly. Therefore, it is possible to calculate the oxygen saturation based on the signal ratio of the image signals.

SUMMARY OF THE INVENTION

In the case of emitting first signal light and second signal light to the observation target at different timings as in JP2012-100800A, JP2012-130429A, and JP2013-099464A, it is possible to calculate the oxygen saturation most accurately when there is no movement of the observation target between timings at which image signals corresponding to the first signal light and the second signal light are acquired. However, the observation target is a living body, such as an esophagus, a stomach, or an intestine, for example. Usually, the living body, such as an esophagus, a stomach, or an intestine, almost continuously moves due to peristaltic movement or the like even while performing observation with an endoscope system. In addition, even if there is no movement of the observation target itself, if there is a movement of an endoscope, for example, when the operator moves the endoscope, this is equivalent to there being a relative movement of the observation target.

If there is a movement of the observation target or the endoscope, a position shift may occur between frames to acquire image signals corresponding to the first signal light and the second signal light. In addition, emission angles of first illumination light and second illumination light to the observation target may be changed due to the movement of the observation target or the endoscope, and accordingly, the light amount ratio of reflected light of the first illumination light and reflected light of the second illumination light may change. The position shift or the change in the light amount ratio degrades the calculation accuracy of the oxygen saturation. That is, robustness against the movement of the observation target or the endoscope is low.

It is an object of the invention to provide an endoscope system capable of accurately calculating the oxygen saturation even if there is a movement of an observation target or an endoscope by increasing the robustness against the movement of the observation target or the endoscope, a processor device for an endoscope system, an operation method for an endoscope system, and an operation method for a processor device.

An endoscope system of the invention includes: a light source that emits first illumination light and second illumination light having different emission spectrums; an imaging device that images an observation target under illumination with the first illumination light and outputs a first image signal and images the observation target under illumination with the second illumination light and outputs a second image signal; a movement amount calculation unit that calculates a movement amount of the observation target based on the first or second image signal; and an oxygen saturation calculation unit that calculates an oxygen saturation based on the movement amount in at least one of a first mode, in which the oxygen saturation is calculated using the first and second image signals, and a second mode, in which the oxygen saturation is calculated using the first image signal.

For example, the movement amount calculation unit calculates one movement amount in an entire imaging region, and the first and second modes are changed at once in the entire imaging region.

The movement amount calculation unit may divide an imaging region into a plurality of regions and calculate the movement amount for each of the regions. The oxygen saturation calculation unit may calculate the oxygen saturation in the first mode for the region where the movement amount falls within a specific range set in advance, and may calculate the oxygen saturation in the second mode for the region where the movement amount does not fall within the specific range. In this case, the movement amount calculation unit may calculate the movement amount for each pixel of the first or second image signal.

It is preferable that, when calculating the oxygen saturation in each of the first and second modes, the oxygen saturation calculation unit include a first mode image generation unit that generates a first mode image as an oxygen saturation image showing an oxygen saturation calculated in the first mode, a second mode image generation unit that generates a second mode image as an oxygen saturation image showing an oxygen saturation calculated in the second mode, and a weighting combination unit that generates a composite oxygen saturation image by giving a weighting corresponding to the movement amount to each of the first and second mode images and combining the weighted first and second mode images.

The endoscope system may further include a light source control unit that performs control to emit the first illumination light and the second illumination light alternately in both of the first and second modes by controlling light emission timings of the first illumination light and the second illumination light.

In addition, the endoscope system may further include a light source control unit that performs control to emit the first illumination light and the second illumination light alternately in the first mode and emit only the first illumination light in the second mode by controlling light emission timings of the first illumination light and the second illumination light.

The movement amount calculation unit may calculate the movement amount based on a ratio between a red image signal included in the first image signal and a red image signal included in the second image signal.

The first mode is a mode in which the oxygen saturation is calculated based on a ratio between a blue image signal included in the first image signal and a green image signal included in the second image signal, for example. The second mode is a mode in which the oxygen saturation is calculated based on a ratio between blue and green image signals included in the first image signal, for example.

A processor device of the invention is a processor device for an endoscope system including a light source that emits first illumination light and second illumination light having different emission spectrums and an imaging device that images an observation target under illumination with the first illumination light and outputs a first image signal and images the observation target under illumination with the second illumination light and outputs a second image signal. The processor device for an endoscope system includes: a reception unit that receives the first and second image signals; a movement amount calculation unit that calculates a movement amount of the observation target based on the first or second image signal; and an oxygen saturation calculation unit that calculates an oxygen saturation based on the movement amount in at least one of a first mode, in which the oxygen saturation is calculated using the first and second image signals, and a second mode, in which the oxygen saturation is calculated using the first image signal.

An operation method for an endoscope system of the invention includes: a step of emitting first illumination light and second illumination light having different emission spectrums using a light source and imaging an observation target under illumination with the first illumination light and outputting a first image signal and imaging the observation target under illumination with the second illumination light and outputting a second image signal using an imaging device; a step of calculating a movement amount of the observation target based on the first or second image signal using a movement amount calculation unit; and a step of calculating an oxygen saturation based on the movement amount in at least one of a first mode, in which the oxygen saturation is calculated using the first and second image signals, and a second mode, in which the oxygen saturation is calculated using the first image signal, using an oxygen saturation calculation unit.

An operation method for a processor device of the invention is an operation method for a processor device used in an endoscope system including a light source that emits first illumination light and second illumination light having different emission spectrums and an imaging device that images an observation target under illumination with the first illumination light and outputs a first image signal and images the observation target under illumination with the second illumination light and outputs a second image signal. The operation method for a processor device includes: a step of receiving the first and second image signals using a reception unit; a step of calculating a movement amount of the observation target based on the first or second image signal using a movement amount calculation unit; and a step of calculating an oxygen saturation based on the movement amount in at least one of a first mode, in which the oxygen saturation is calculated using the first and second image signals, and a second mode, in which the oxygen saturation is calculated using the first image signal, using an oxygen saturation calculation unit.

According to the endoscope system, the processor device for an endoscope system, the operation method for an endoscope system, and the operation method for a processor device of the invention, it is possible to accurately calculate the oxygen saturation even if there is a movement of the observation target or the endoscope. That is, it is possible to increase the robustness against the movement of the observation target or the endoscope.

DESCRIPTION OF THE PREFERRED EMBODIMENTS

[First Embodiment]

Figure 1:
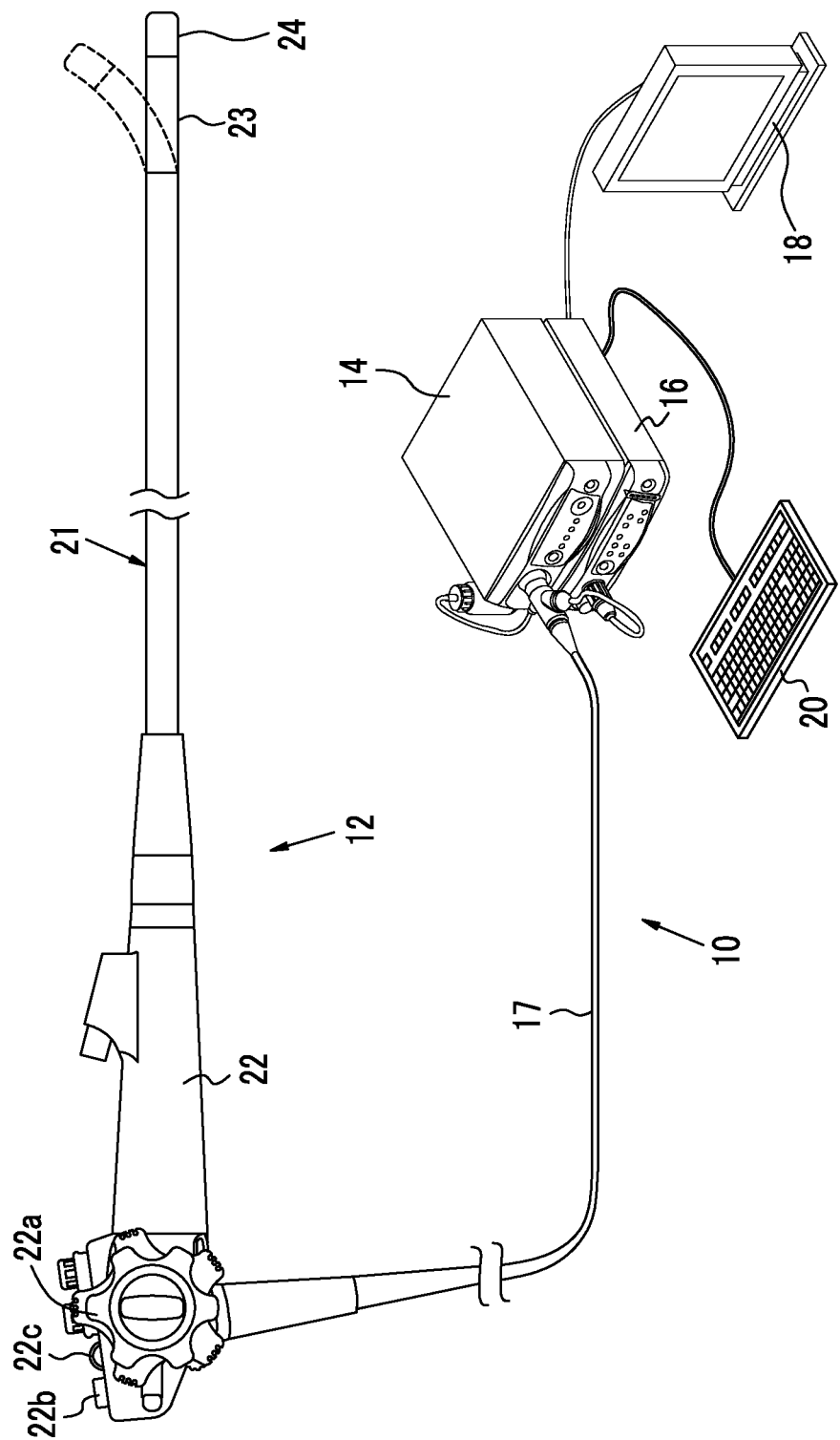
FIG. 1 is an external view of an endoscope system.

As shown in FIG. 1, an endoscope system 10 according to a first embodiment includes an endoscope 12, a light source device 14, a processor device 16, a monitor 18 (display unit), and a console 20. The endoscope 12 is optically connected to the light source device 14, and is electrically connected to the processor device 16. The endoscope 12 includes an inserted portion 21 that is inserted into a subject, an operating portion 22 provided at the base end of the inserted portion 21, and a bending portion 23 and a distal portion 24 that are provided at the distal side of the inserted portion 21. By operating an angle knob 22a of the operating portion 22, the bending portion 23 is bent. The distal portion 24 can be directed in a desired direction by the bending operation.

In addition to the angle knob 22a, an observation mode selector SW (observation mode selector switch) 22b, a zoom operation portion 22c, and a freeze button (not shown) for saving a still image are provided in the operating portion 22. The mode selector SW 22b is used for a switching operation between two modes of the normal observation mode and the special observation mode. The normal observation mode is a mode in which a normal light image obtained by full-color imaging of the observation target in the subject is displayed on the monitor 18. The special observation mode is a mode in which an oxygen saturation image obtained by imaging the oxygen saturation of blood hemoglobin of the observation target is displayed on the monitor 18. The zoom operation portion 22c is used for a zooming operation for driving a zoom lens 47 (refer to FIG. 2) in the endoscope 12 to magnify the observation target.

The processor device 16 is electrically connected to the monitor 18 and the console 20. The monitor 18 displays an image, such as a normal light image or an oxygen saturation image, and information regarding the image (hereinafter, referred to as image information or the like). The console 20 functions as a user interface (UI) for receiving an input operation, such as a function setting. In addition, a recording unit (not shown) in which image information or the like is recorded may be connected to the processor device 16.

Figure 2:
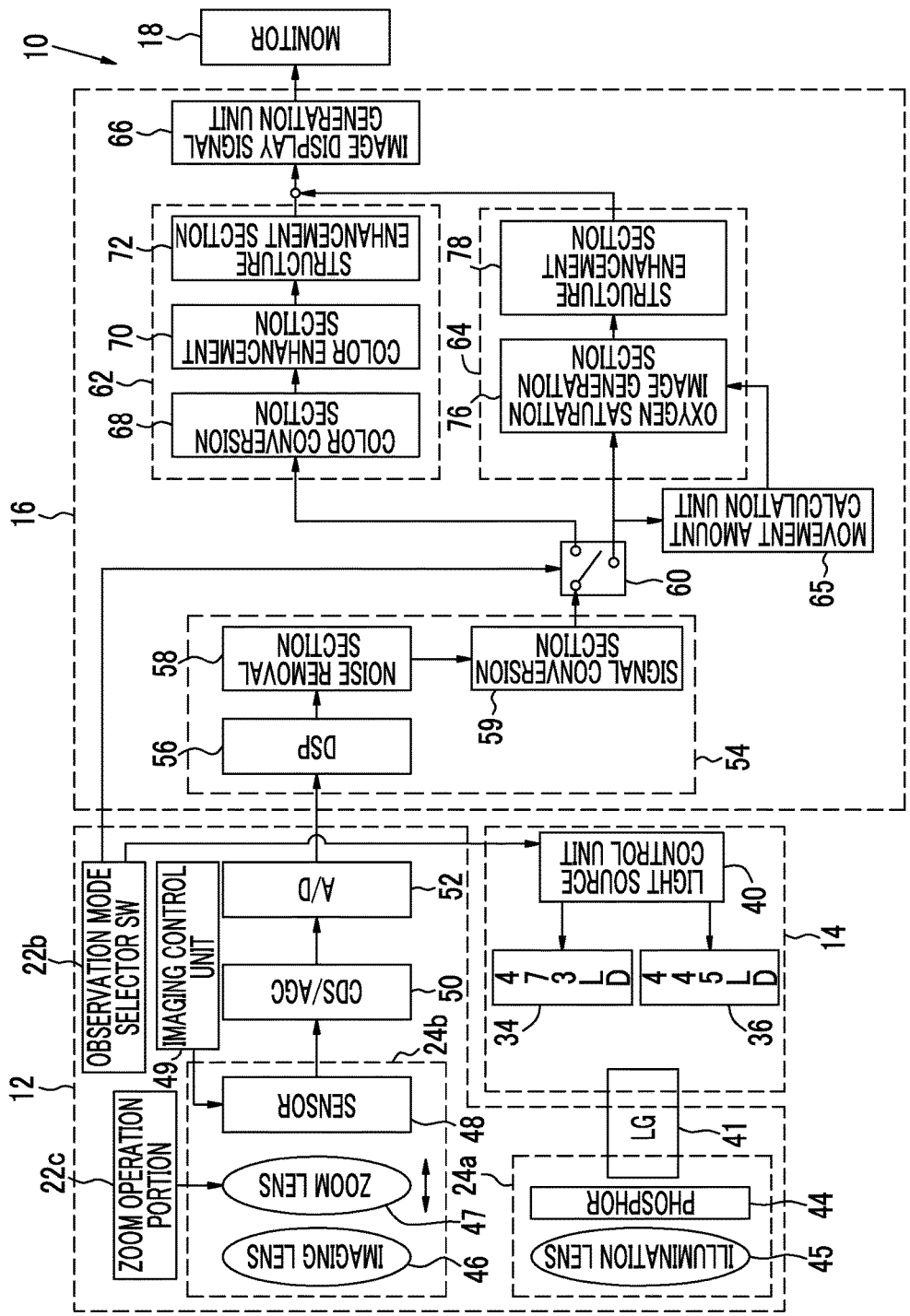
FIG. 2 is a block diagram of the endoscope system.

As shown in FIG. 2, the light source device 14 includes, as light emitting sources, a first blue laser light source (473 LD (laser diode)) 34 that emits first blue laser light having a center wavelength of 473 nm and a second blue laser light source (445 LD) 36 that emits second blue laser light having a center wavelength of 445 nm. The light emission amount and the light emission timing of each of the light sources 34 and 36 formed of the semiconductor light emitting elements are separately controlled by a light source control unit 40. For this reason, the light intensity ratio between light emitted from the first blue laser light source 34 and light emitted from the second blue laser light source 36 can be freely changed. In addition, it is preferable that the half-width of each of the first and second blue laser light beams be set to about ±10 nm. As the first blue laser light source 34 and the second blue laser light source 36, a broad area type InGaN-based laser diode can be used, or an InGaNAs-based laser diode or a GaNAs-based laser diode can be used. In addition, as the light sources, it is possible to use a structure using a light emitter, such as a light emitting diode.

The light source control unit 40 turns on the second blue laser light source 36 in the normal observation mode. On the other hand, in the special observation mode, the light source control unit 40 turns on the first blue laser light source 34 and the second blue laser light source 36 alternately at intervals of one frame.

The first and second blue laser light beams emitted from the light sources 34 and 36 are incident on a light guide (LG) 41 through optical members, such as a condensing lens, an optical fiber, and a multiplexer (none are shown). The light guide 41 is built into a universal cord 17 that connects the endoscope 12 and the light source device 14 to each other (refer to FIG. 1) and the endoscope 12. The light guide 41 causes the first and second blue laser light beams to propagate from the light sources 34 and 36 to the distal portion 24 of the endoscope 12 therethrough. As the light guide 41, a multi-mode fiber can be used. As an example, it is possible to use a small-diameter fiber cable having a diameter of ϕ0.3 mm to ϕ0.5 mm that includes a core with a diameter of 105 μm, a cladding with a diameter of 125 μm, and a protective layer as an outer skin.

The distal portion 24 of the endoscope 12 includes an illumination optical system 24a and an imaging optical system 24b. A phosphor 44 and an illumination lens 45 are provided in the illumination optical system 24a. The first and second blue laser light beams are incident on the phosphor 44 from the light guide 41. The phosphor 44 emits fluorescence due to the first or second blue laser light emitted thereto. Some of the first or second blue laser light beams are transmitted through the phosphor 44. The light emitted from the phosphor 44 is emitted to the observation target through the illumination lens 45. Accordingly, the first blue laser light source 34, the second blue laser light source 36, and the phosphor 44 form a light source that emits illumination light to the observation target.

Figure 3:
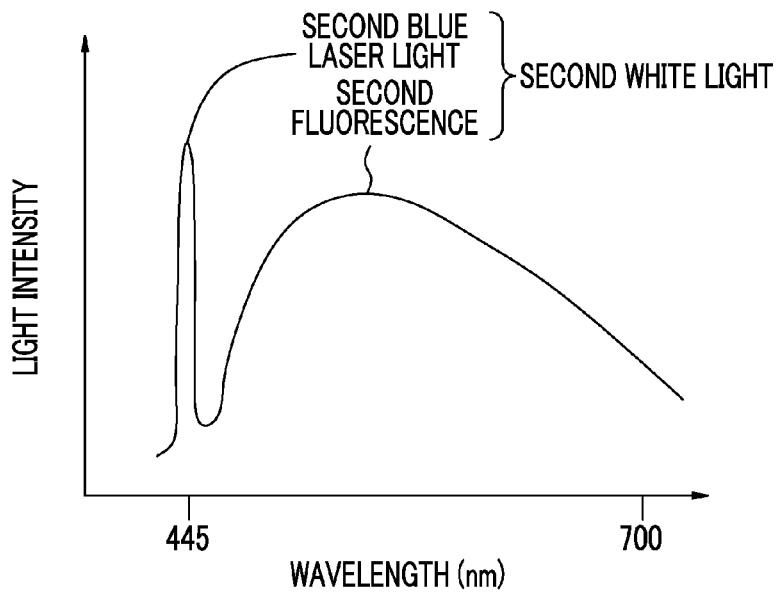
FIG. 3 is a graph showing the spectrum of light emitted in a normal observation mode.

In the normal observation mode, the second blue laser light is incident on the phosphor 44. Accordingly, white light having a spectrum shown in FIG. 3 (hereinafter, referred to as second white light) is emitted to the observation target as illumination light. The second white light is configured to include second blue laser light and second fluorescence of green to red that is excited and emitted from the phosphor 44 by the second blue laser light. Accordingly, the wavelength range of the second white light is the entire visible light region.

Figure 4:
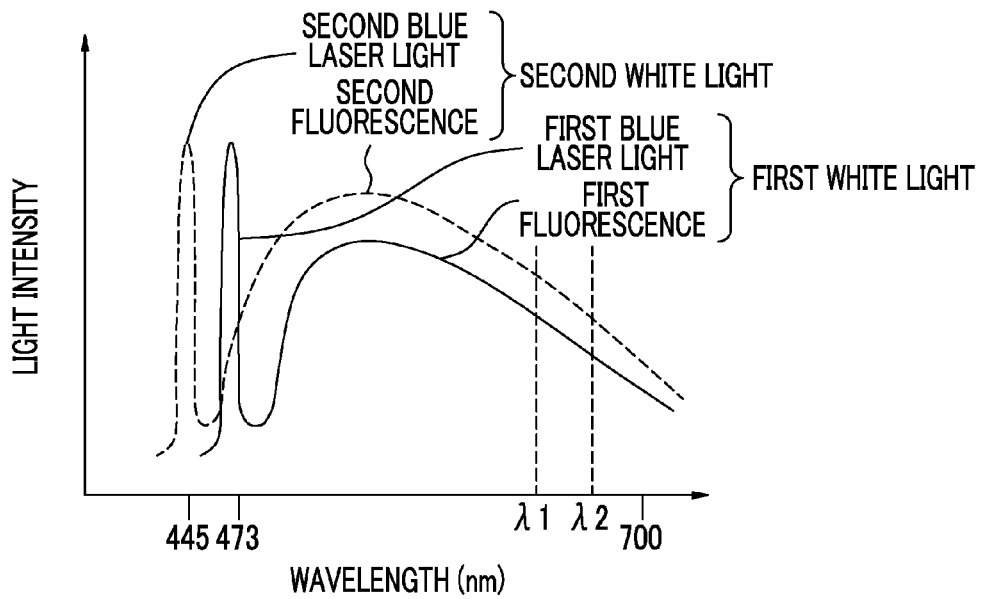
FIG. 4 is a graph showing the spectrum of light emitted in a special observation mode.

On the other hand, in the special observation mode, the first blue laser light and the second blue laser light are alternately incident on the phosphor 44. Therefore, as shown in FIG. 4, first white light and second white light having different emission spectrums are alternately emitted to the observation target as illumination light. The first white light is configured to include first blue laser light and first fluorescence of green to red that is excited and emitted from the phosphor 44 by the first blue laser light. Accordingly, the wavelength range of the first white light is the entire visible light region. The second white light is the same as the second white light emitted in the normal observation mode. In the present embodiment, the first white light is first illumination light, and the second white light is second illumination light.

The first fluorescence and the second fluorescence have almost the same waveform (shape of the spectrum), and the ratio between the intensity (I1 ($\lambda$)) of the first fluorescence and the intensity (I2 ($\lambda$)) of the second fluorescence (hereinafter, referred to as an inter-frame intensity ratio) is the same at any wavelength $\lambda$. For example, it is I2 ($\lambda$1)/I1 ($\lambda$1)=I2 ($\lambda$2)/I1 ($\lambda$2). Since the inter-frame intensity ratio I2 ($\lambda$)/I1 ($\lambda$) affects the calculation accuracy of the oxygen saturation, the inter-frame intensity ratio I2 ($\lambda$)/I1 ($\lambda$) is accurately controlled by the light source control unit 40 such that the intensity ratio between reference frames set in advance is maintained.

As the phosphor 44, it is preferable to use a phosphor that absorbs some of the first and second blue laser light beams and includes a plurality of kinds of phosphors (for example, a YAG-based phosphor or a phosphor, such as BAM ($BaMgAl_{10}O_{17}$)) that are excited to emit green to red light beams. If a semiconductor light emitting element is used as a light source for exciting the phosphor 44 as in the present embodiment, it is possible to obtain high-intensity first and second white light beams with high luminous efficiency. In addition, it is possible to easily adjust the intensity of the white light and to suppress changes in color temperature and chromaticity.

The imaging optical system 24b of the endoscope 12 includes an imaging lens 46, the zoom lens 47, and a sensor 48 (refer to FIG. 2). Reflected light from the observation target is incident on the sensor 48 through the imaging lens 46 and the zoom lens 47. Then, a reflected image of the observation target is formed on the sensor 48. The zoom lens 47 is moved between the tele end and the wide end by operating the zoom operation portion 22c. When the zoom lens 47 is moved to the tele end side, the reflected image of the observation target is magnified. On the other hand, when the zoom lens 47 is moved to the wide end side, the reflected image of the observation target is reduced. In addition, when magnified observation is not performed (at the time of non-magnified observation), the zoom lens 47 is disposed at the wide end. When performing magnified observation, the zoom lens 47 is moved from the wide end to the tele end side by operating the zoom operation portion 22c.

The sensor 48 is a color imaging device, and captures a reflected image of the observation target and outputs the image signal. As the sensor 48, for example, a charge coupled device (CCD) image sensor or a complementary metal oxide semiconductor (CMOS) image sensor can be used. In the present embodiment, the sensor 48 is a CCD image sensor. In addition, the sensor 48 includes RGB pixels in which RGB color filters are provided on the imaging surface, and outputs image signals of three colors of R, G, and B by performing photoelectric conversion in the pixels of respective colors of RGB.

Figure 5:
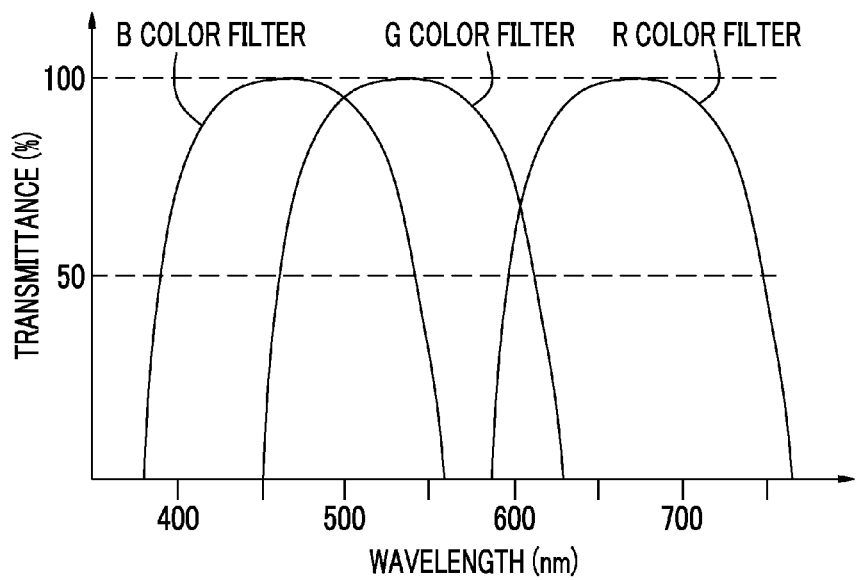
FIG. 5 is a graph showing the spectral transmittance of an RGB color filter.

As shown in FIG. 5, the B color filter has a spectral transmittance of 380 nm to 560 nm, the G color filter has a spectral transmittance of 450 nm to 630 nm, and the R color filter has a spectral transmittance of 580 nm to 760 nm. Accordingly, when the second white light is emitted to the observation target in the normal observation mode, the second blue laser light and some of green components of the second fluorescence are incident on the B pixel, some of green components of the second fluorescence are incident on the G pixel, and red components of the second fluorescence are incident on the R pixel. In the B image signal output from the B pixel, the emission intensity of the second blue laser light is significantly larger than that of the second fluorescence. Accordingly, most of the B image signal is occupied by the reflected light components of the second blue laser light.

On the other hand, when the first white light is emitted to the observation target in the special observation mode, the first blue laser light and some of green components of the first fluorescence are incident on the B pixel, some of green components of the first fluorescence and the first blue laser light attenuated by the G color filter are incident on the G pixel, and red components of the first fluorescence are incident on the R pixel. Since the emission intensity of the first blue laser light is significantly larger than that of the first fluorescence, most of the B image signal output from the B pixel is occupied by the reflected light components of the first blue laser light.

Light incidence components in the respective RGB pixels when the second white light is emitted to the observation target in the special observation mode are the same as those in the normal observation mode.

As the sensor 48, it is also possible to use a so-called complementary color image sensor including complementary color filters of C (cyan), M (magenta), Y (yellow), and G (green) on the imaging surface. When using the complementary color image sensor as the sensor 48, a color converter that performs color conversion from image signals of four colors of CMYG to image signals of three colors of RGB is preferably provided in the endoscope 12, the light source device 14, or the processor device 16. In this manner, even when complementary color image sensors are used, it is possible to obtain the image signals of three colors of RGB from the image signals of four colors of CMYG by color conversion.

Figure 6:
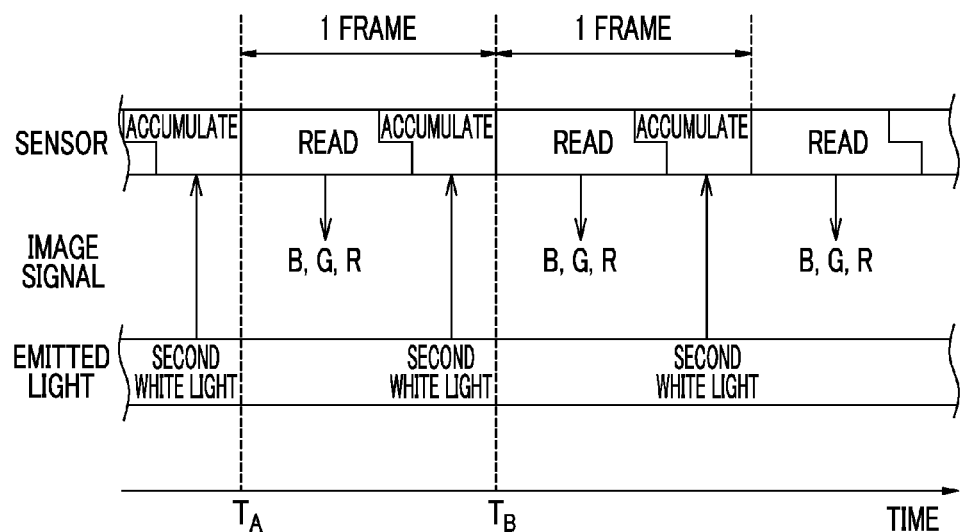
FIG. 6 is an explanatory diagram showing imaging control in the normal observation mode.

An imaging control unit 49 performs imaging control of the sensor 48. As shown in FIG. 6, in the normal observation mode, an observation target illuminated by the second white light is imaged by the sensor 48 every period of one frame (hereinafter, simply referred to as one frame). Then, the image signals of RGB are output from the sensor 48 for each frame. In the present embodiment, the sensor 48 is a CCD image sensor. Accordingly, one frame is a period of the length from the end (time $T_A$) of a charge accumulation period (also referred to as an exposure period) to the end of the next charge accumulation period (time $T_B$), for example. In addition, since the sensor 48 is a CCD image sensor, one frame is divided into a reading period and a charge accumulation period in FIG. 6. However, the approximately entire one frame can be set as a charge accumulation period, and signal charges accumulated in the previous frame can also be read during the accumulation of signal charges. The imaging control unit 49 also performs control, such as the adjustment of the length of the charge accumulation period.

Figure 7:
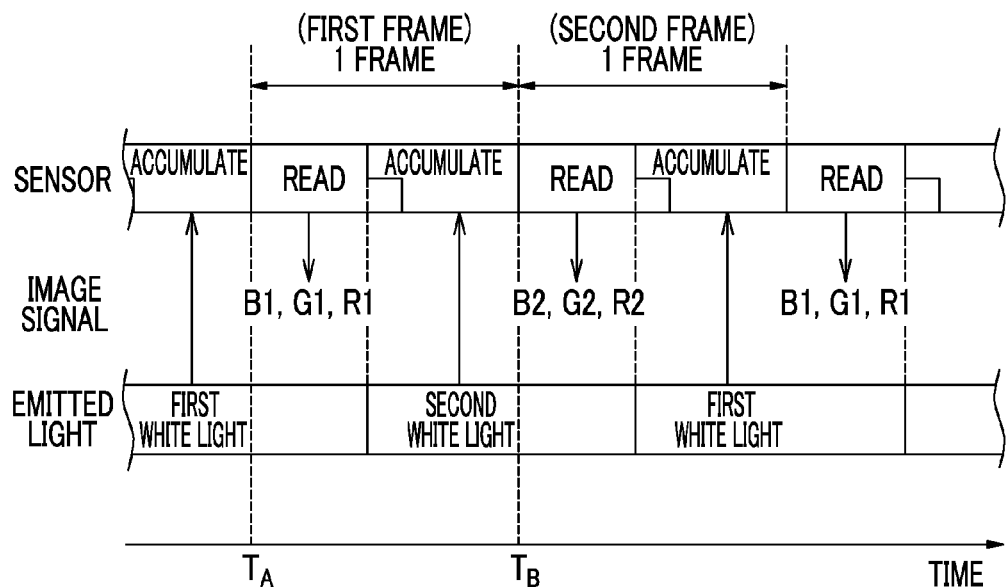
FIG. 7 is an explanatory diagram showing imaging control in the special observation mode.

Also in the special observation mode, the imaging control unit 49 performs imaging control of the sensor 48 in the same manner as in the normal observation mode. However, in the special observation mode, the first white light and the second white light are alternately emitted to the observation target in synchronization with the imaging frame of the sensor 48. Therefore, as shown in FIG. 7, the sensor 48 reads signal charges, which are obtained by imaging the observation target under the first white light, to the reading period of the first frame, and outputs the image signals of RGB colors. Then, the sensor 48 reads signal charges, which are obtained by imaging the observation target under the second white light, to the reading period of the second frame, and outputs the image signals of RGB colors. The sensor 48 outputs the image signals of RGB colors in both the first and second frames. However, the spectrum of white light in the first frame and the spectrum of white light in the second frame are different. Therefore, for the sake of distinction, the image signals of RGB colors that the sensor 48 outputs in the first frame are referred to as an R1 image signal, a G1 image signal, and a B1 image signal, and the image signals of RGB colors that the sensor 48 outputs in the second frame are referred to as an R2 image signal, a G2 image signal, and a B2 image signal. In addition, the B1 image signal, the G1 image signal, and the R1 image signal output in the first frame are referred to as a first image signal, and the B2 image signal, the G2 image signal, and the R2 image signal output in the second frame are referred to as a second image signal.

In addition, in order to calculate the oxygen saturation, for example, a signal ratio B1/G2 between the B1 image signal and the G2 image signal and a signal ratio R2/G2 between the R2 image signal and the G2 image signal are used. Between these signal ratios, the signal ratio B1/G2 between the B1 image signal and the G2 image signal is a signal ratio that is required for the calculation of the oxygen saturation. For this reason, a component (first blue laser light transmitted through the phosphor 44) that becomes the B1 image signal in the first white light is the first signal light, and a component (green band component of the second fluorescence) that becomes the G2 image signal in the second white light is the second signal light. In the endoscope system 10, a signal ratio B1/G1 between the B1 image signal and the G1 image signal and a signal ratio R1/G1 between the R1 image signal and the G1 image signal may be used. In this case, a component that becomes the B1 image signal in the first white light is the first signal light, and a component (green band component of the first fluorescence) that becomes the G1 image signal in the first white light is the second signal light.

The image signals of the respective colors output from the sensor 48 are transmitted to a correlated double sampling (CDS)/automatic gain control (AGC) circuit 50 (refer to FIG. 2). The CDS/AGC circuit 50 performs correlated double sampling (CDS) or automatic gain control (AGC) for the analog image signals output from the sensor 48. The image signals transmitted through the CDS/AGC circuit 50 are converted into digital image signals by an A/D converter 52. The image signals that have been digitized in this manner are input to the processor device 16.

The processor device 16 includes a receiving unit 54, an image processing switching unit 60, a normal observation image processing unit 62, a special observation image processing unit 64, a movement amount calculation unit 65, and an image display signal generation unit 66. The receiving unit 54 receives the image signal input from the endoscope 12. The receiving unit 54 includes a digital signal processor (DSP) 56, a noise removal section 58, and a signal conversion section 59.

The DSP 56 performs various kinds of signal processing, such as defect correction processing, offset processing, gain correction processing, linear matrix processing, gamma conversion processing, demosaic processing, and YC conversion processing, on the received image signal. By the defect correction processing, the signal of the defective pixel of the sensor 48 is corrected. By the offset processing, a dark current component is removed from the image signal subjected to the defect correction processing, and the accurate zero level is set. In the gain correction processing, the signal level of each image signal is adjusted by multiplying each of the RGB image signals after the offset processing by a specific gain. Linear matrix processing for increasing color reproducibility is performed on the image signal of each color after the gain correction processing. Then, the brightness or saturation of each image signal is adjusted by gamma conversion processing. Demosaic processing (also referred to as isotropic processing or synchronization processing) is performed on the image signal after the linear matrix processing, and the signal of missing color of each pixel is generated by interpolation. Through the demosaic processing, all pixels have signals of RGB colors. The signal conversion section 59 performs YC conversion processing on each image signal after the demosaic processing, and outputs a brightness signal Y and color difference signals Cb and Cr to the noise removal section 58.

The noise removal section 58 performs noise removal processing using, for example, a moving average method or a median filter method on the image signal subjected to the demosaic processing or the like by the DSP 56. The image signals after noise has been removed are input to the signal conversion section 59, are reconverted into RGB image signals, and are input to the image processing switching unit 60.

When the observation mode selector SW 22*b* is set to the normal observation mode, the image processing switching unit 60 inputs the image signals to the normal observation image processing unit 62. On the other hand, when the observation mode selector SW 22*b* is set to the special observation mode, the image processing switching unit 60 inputs the image signals to the special observation image processing unit 64 and the movement amount calculation unit 65.

The normal observation image processing unit 62 includes a color conversion section 68, a color enhancement section 70, and a structure enhancement section 72. The color conversion section 68 generates RGB image data by assigning the input RGB image signals of one frame to R, G, and B pixels. Then, color conversion processing, such as 3×3 matrix processing, gradation conversion processing, and three-dimensional LUT processing, is performed on the RGB image data.

The color enhancement section 70 performs various kinds of color enhancement processing on the RGB image data after the color conversion processing. The structure enhancement section 72 performs structure enhancement processing, such as spatial frequency enhancement, on the RGB image data after the color enhancement processing. The RGB image data subjected to the structure enhancement processing by the structure enhancement section 72 is input to the image display signal generation unit 66 as a normal observation image.

The special observation image processing unit 64 includes an oxygen saturation image generation section 76 and a structure enhancement section 78. The oxygen saturation image generation section 76 calculates the oxygen saturation, and generates an oxygen saturation image indicating the calculated oxygen saturation.

The structure enhancement section 78 performs structure enhancement processing, such as spatial frequency enhancement processing, on the oxygen saturation image input from the oxygen saturation image generation section 76. The oxygen saturation image subjected to the structure enhancement processing by the structure enhancement section 72 is input to the image display signal generation unit 66.

When the observation mode selector SW 22*b* is set to the special observation mode, the movement amount calculation unit 65 acquires an image signal from the image processing switching unit 60 and calculates a movement amount using the acquired image signal. For example, the movement is a change in movement, deformation, rotation, and direction due to peristaltic movement of the observation target, a relative change of the observation target due to changes in the movement, rotation, and direction of the distal portion 24 inside the subject, or an overall change of the observation target due to the combination result of the change of the observation target itself and the relative change of the observation target due to the change of the distal portion 24. In addition, the movement amount is a value indicating the magnitude of such movement of the observation target.

The movement amount calculation unit 65 calculates the movement amount based on the signal ratio between the R1 image signal acquired in the first frame and the R2 image signal acquired in the second frame. Specifically, the movement amount calculation unit 65 calculates the ratio between the signal values of the R1 image signal and the R2 image signal for each pixel and sets the average value as the movement amount, for example. Therefore, in the entire imaging region expressed by the first image signal (or the second image signal), one movement amount is calculated by the movement amount calculation unit 65. Needless to say, other statistical values, such as a total value, a maximum value, a minimum value, a median, and a variance of the ratio between the signal values of the R1 image signal and the R2 image signal, can also be used as the movement amount. When there is no movement of the observation target, the R1 image signal and the R2 image signal are almost the same. In this case, therefore, the movement amount is approximately "1". On the other hand, when a movement occurs in the observation target between the first and second frames, a difference occurs between the R1 image signal and the R2 image signal. In this case, the movement amount becomes a value shifted from "1". The shift of the movement amount from "1" increases as the movement of the observation target increases.

The movement amount calculation unit 65 inputs the calculated movement amount to the oxygen saturation image generation section 76. The oxygen saturation image generation section 76 has first and second modes as modes for calculating the oxygen saturation, and calculates the oxygen saturation in at least one of the modes based on the movement amount input from the movement amount calculation unit 65. The first mode is a mode in which the oxygen saturation is calculated based on both of the first image signal, which is acquired in the first frame by imaging the observation target under illumination with the first white light, and the second image signal, which is acquired in the second frame by imaging the observation target under illumination with the second white light. More specifically, in the first mode, the oxygen saturation is calculated based on the signal ratio B1/G2 between the B1 image signal and the G2 image signal and the signal ratio R2/G2 between the R2 image signal and the G2 image signal. On the other hand, the second mode is a mode in which the oxygen saturation is calculated based on only the first image signal without using the second image signal. More specifically, in the second mode, the oxygen saturation is calculated based on the signal ratio B1/G1 between the B1 image signal and the G1 image signal and the signal ratio R1/G1 between the R1 image signal and the G1 image signal.

The image display signal generation unit 66 converts the normal observation image or the oxygen saturation image into a display format signal (display image signal), and inputs the display format signal to the monitor 18. As a result, the normal observation image or the oxygen saturation image is displayed on the monitor 18.

Figure 8:
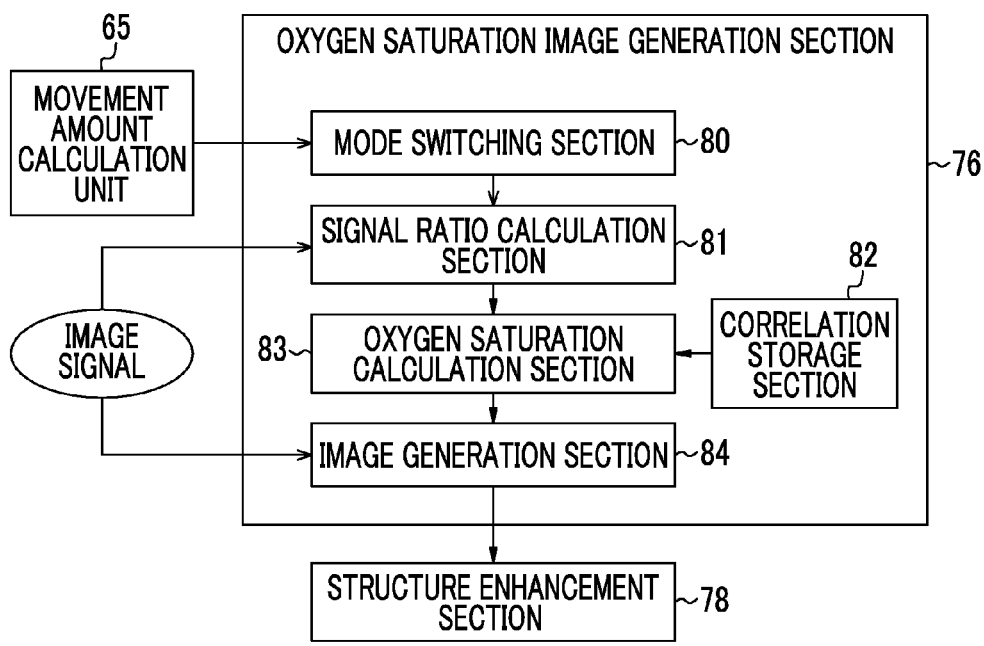
FIG. 8 is a block diagram of an oxygen saturation image generation section.

As shown in FIG. 8, the oxygen saturation image generation section 76 includes a mode switching section 80, a signal ratio calculation section 81, a correlation storage section 82, an oxygen saturation calculation section 83, and an image generation section 84.

The mode switching section 80 compares the movement amount input from the movement amount calculation unit 65 with a threshold value (a set of upper and lower limit values determining the range of the movement amount), and inputs a mode setting signal for switching the mode to calculate the oxygen saturation to the signal ratio calculation section 81 according to the result. Specifically, when it is determined that the movement amount falls within the specific range determined by the threshold value and accordingly the movement of the observation target is small, a mode setting signal for setting the mode to calculate the oxygen saturation to the first mode is input to the signal ratio calculation section 81. On the other hand, when it is determined that the movement amount does not fall within the specific range determined by the threshold value and accordingly the movement of the observation target is large, a mode setting signal for setting the mode to calculate the oxygen saturation to the second mode is input to the signal ratio calculation section 81. In addition, the threshold value and the specific range determined by the threshold value are determined in advance by setting or the like. In addition, since one movement amount is calculated in the entire imaging region expressed by the first image signal (or the second image signal), the calculation mode switching of the mode switching section 80 is performed at once in the entire imaging region based on the one movement amount.

The signal ratio calculation section 81 calculates a signal ratio used in the oxygen saturation calculation section 83 according to the mode setting signal input from the mode switching section 80. When the first mode is set, the signal ratio calculation section 81 calculates the signal ratio B1/G2 between the B1 image signal and the G2 image signal for each pixel, and calculates the signal ratio R2/G2 between the R2 image signal and the G2 image signal for each pixel. When calculating the signal ratio B1/G2, the signal ratio calculation section 81 uses the B1 image signal that is corrected to the signal value mostly based on only the first blue laser light by performing correction processing for enhancing the color separability by removing the signal value based on the first fluorescence from the B1 image signal by inter-pixel calculation using the B1 image signal, the G1 image signal, and the R1 image signal.

On the other hand, when the second mode is set, the signal ratio calculation section 81 calculates the signal ratio B1/G1 between the B1 image signal and the G1 image signal for each pixel, and calculates the signal ratio R1/G1 between the R1 image signal and the G1 image signal for each pixel. When calculating the signal ratios B1/G1 and R1/G1, the signal ratio calculation section 81 performs correction processing for enhancing the color separability by removing the signal value based on the first fluorescence from the B1 image signal and removing the signal value based on the first laser light from the G1 image signal by inter-pixel calculation using the B1 image signal, the G1 image signal, and the R1 image signal. Then, the signal ratio B1/G1 and the signal ratio R1/G1 are calculated using the B1 image signal, which has been corrected so as to have a signal value based on almost only the first blue laser light, and the G1 image signal, which has been corrected so as to have a signal value based on almost only the first fluorescence.

When the first and second modes are compared, in the first mode, only the B1 image signal is corrected when calculating the signal ratio used for the calculation of the oxygen saturation. Therefore, the accuracy of the oxygen saturation in the first mode is higher than that in the second mode in which two kinds of image signals of the B1 image signal and the G1 image signal are corrected. On the other hand, in the second mode, the oxygen saturation is calculated using only the first image signals acquired at the same time in one frame (first frame). Therefore, even if there is a movement of the observation target, the calculation accuracy of the oxygen saturation is not reduced.

Figure 9:
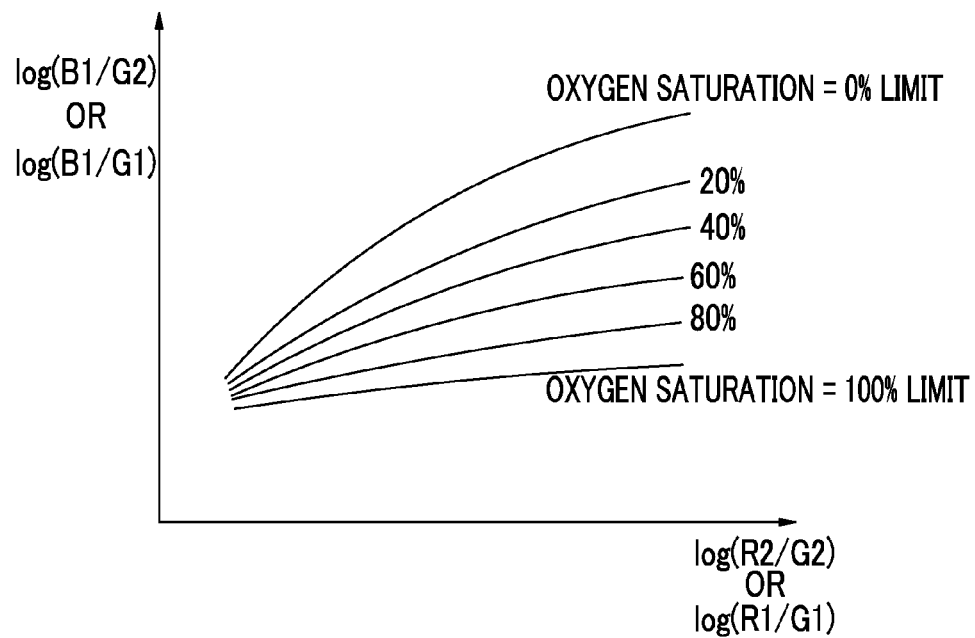
FIG. 9 is a graph showing the correlation between the signal ratio and the oxygen saturation.

The correlation storage section 82 stores the correlation between the oxygen saturation and a set of two signal ratios calculated in the respective modes by the signal ratio calculation section 81. This correlation is stored in a two-dimensional table that defines the isolines of the oxygen saturation on a two-dimensional space shown in FIG. 9. In the present embodiment, the correlation is used commonly in the first and second modes. The position and shape of the isolines for the signal ratio are obtained in advance by physical simulation of light scattering, and the distance between isolines changes according to the blood volume (horizontal axis in FIG. 9). In addition, the correlation between the signal ratio and the oxygen saturation is stored in a log scale.

Figure 10:
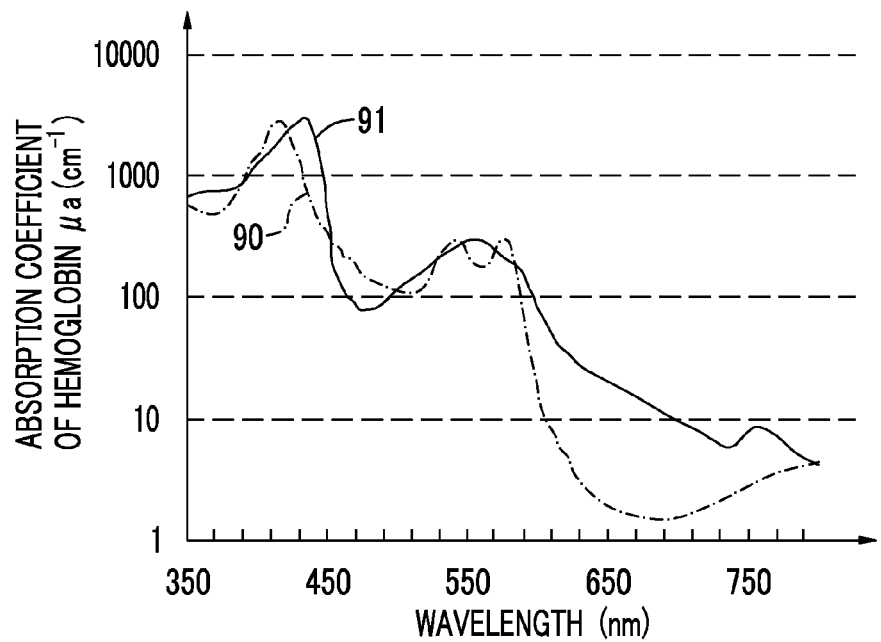
FIG. 10 is a graph showing the light absorption coefficients of oxygenated hemoglobin and reduced hemoglobin.

As shown in FIG. 10, this correlation is closely related to the absorption characteristics or light scattering characteristics of oxygenated hemoglobin (graph 90) or reduced hemoglobin (graph 91). For example, as at a center wavelength of 473 nm of the first blue laser light, at a wavelength at which the difference between the light absorption coefficient of oxygenated hemoglobin and the light absorption coefficient of reduced hemoglobin is large, it is easy to handle the information of the oxygen saturation. However, the B1 image signal including a signal corresponding to 473-nm light has a high dependence not only on the oxygen saturation but also on the blood volume. Therefore, in the first mode, by using the signal ratio R2/G2 obtained from the R2 image signal and the G2 image signal as well as the B1 image signal, it is possible to accurately calculate the oxygen saturation without depending on the blood volume. Here, the R2 image signal corresponds to light that changes mainly depending on the blood volume, and the G2 image signal is a reference signal of the B1 image signal and the R2 image signal. In the second mode, using the G1 image signal as a reference signal of the B1 image signal and the R1 image signal, the signal ratio R1/G1 is used as a signal ratio indicating the blood volume. By using the signal ratio R1/G1, it is possible to accurately calculate the oxygen saturation without depending on the blood volume in the same manner as in the first mode.

Figure 11:
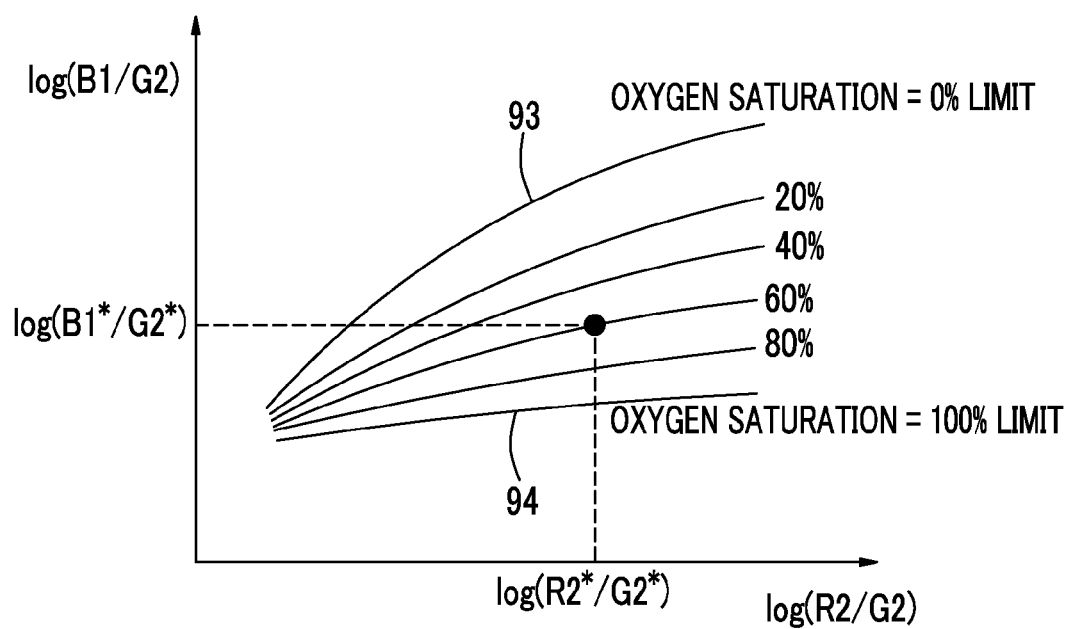
FIG. 11 is an explanatory diagram showing a method of calculating the oxygen saturation.

By using the signal ratio calculated by the signal ratio calculation section 81, the oxygen saturation calculation section 83 calculates the oxygen saturation based on the amount of movement. More specifically, the oxygen saturation calculation section 83 calculates the oxygen saturation corresponding to the signal ratio calculated by the signal ratio calculation section 81, for each pixel, with reference to the correlation stored in the correlation storage section 82. For example, in the first mode, when the signal ratio B1/G2 and the signal ratio R2/G2 in a specific pixel are B1*/G2* and R2*/G2*, respectively, the oxygen saturation corresponding to the signal ratio B1*/G2* and the signal ratio R2*/G2* is "60%" when the correlation shown in FIG. 11 is referred to. Accordingly, the oxygen saturation calculation section 83 calculates the oxygen saturation of the specified pixel as "60%". The same is true for the case in the second mode.

In the first mode, a case where the signal ratio B1/G2 and the signal ratio R2/G2 become extremely large or extremely small hardly occurs. That is, a case hardly occurs in which the value of the signal ratio B1/G2 or the signal ratio R2/G2 exceeds the lower limit line 93 of the oxygen saturation of 0% or on the contrary becomes lower than the upper limit line 94 of the oxygen saturation of 100%. Here, the oxygen saturation calculation section 83 sets the oxygen saturation to 0% when the calculated oxygen saturation is lower than the lower limit line 93, and sets the oxygen saturation to 100% when the calculated oxygen saturation exceeds the upper limit line 94. In addition, when a point corresponding to the signal ratio B1/G2 and the signal ratio R2/G2 deviates from a region between the lower limit line 93 and the upper limit line 94, display showing that the reliability of the oxygen saturation in the pixel is low may be performed, or the oxygen saturation may not be calculated. The same is true for the case of the second mode.

The image generation section 84 generates an oxygen saturation image by imaging the oxygen saturation using the oxygen saturation calculated by the oxygen saturation calculation section 83. Specifically, in the first mode, the image generation section 84 acquires a B2 image signal, a G2 image signal, and an R2 image signal, and multiplies these image signals by the gain corresponding to the oxygen saturation for each pixel. Then, RGB image data is generated using the B2 image signal, the G2 image signal, and the R2 image signal multiplied by the gain. For example, in a pixel where the corrected oxygen saturation is 60% or more, the image generation section 84 multiplies all of the B2 image signal, the G2 image signal, and the R2 image signal by the same gain "1". In contrast, in a pixel where the corrected oxygen saturation is less than 60%, the image generation section 84 multiplies the B2 image signal by the gain less than "1" and multiplies the G2 image signal and the R2 image signal by the gain of "1" or more. RGB image data generated using the B2 image signal, the G2 image signal, and the R2 image signal after the gain processing is the oxygen saturation image.

In the second mode, the image generation section 84 acquires a B1 image signal, a G1 image signal, and an R1 image signal, and multiplies these image signals by the gain corresponding to the oxygen saturation for each pixel. Then, RGB image data is generated as an oxygen saturation image using the B1 image signal, the G1 image signal, and the R1 image signal multiplied by the gain. The gain multiplication method is the same as that in the case of the first mode.

In the oxygen saturation image generated by the image generation section 84, a high oxygen region (region having an oxygen saturation of 60% to 100%) is expressed in the same color as the normal observation image. On the other hand, a low oxygen region where the oxygen saturation is less than a specific value (region having an oxygen saturation of 0% to 60%) is expressed in a different color (pseudo color) from the normal observation image.

Although the image generation section 84 performs gain multiplication for pseudo coloring only for the low oxygen region in the present embodiment, a gain corresponding to the oxygen saturation may also be multiplied for the high oxygen region so that the entire oxygen saturation image is pseudo-colored. In addition, although the low oxygen region and the high oxygen region are divided at the oxygen saturation of 60%, this boundary can be arbitrarily selected.

Figure 12:
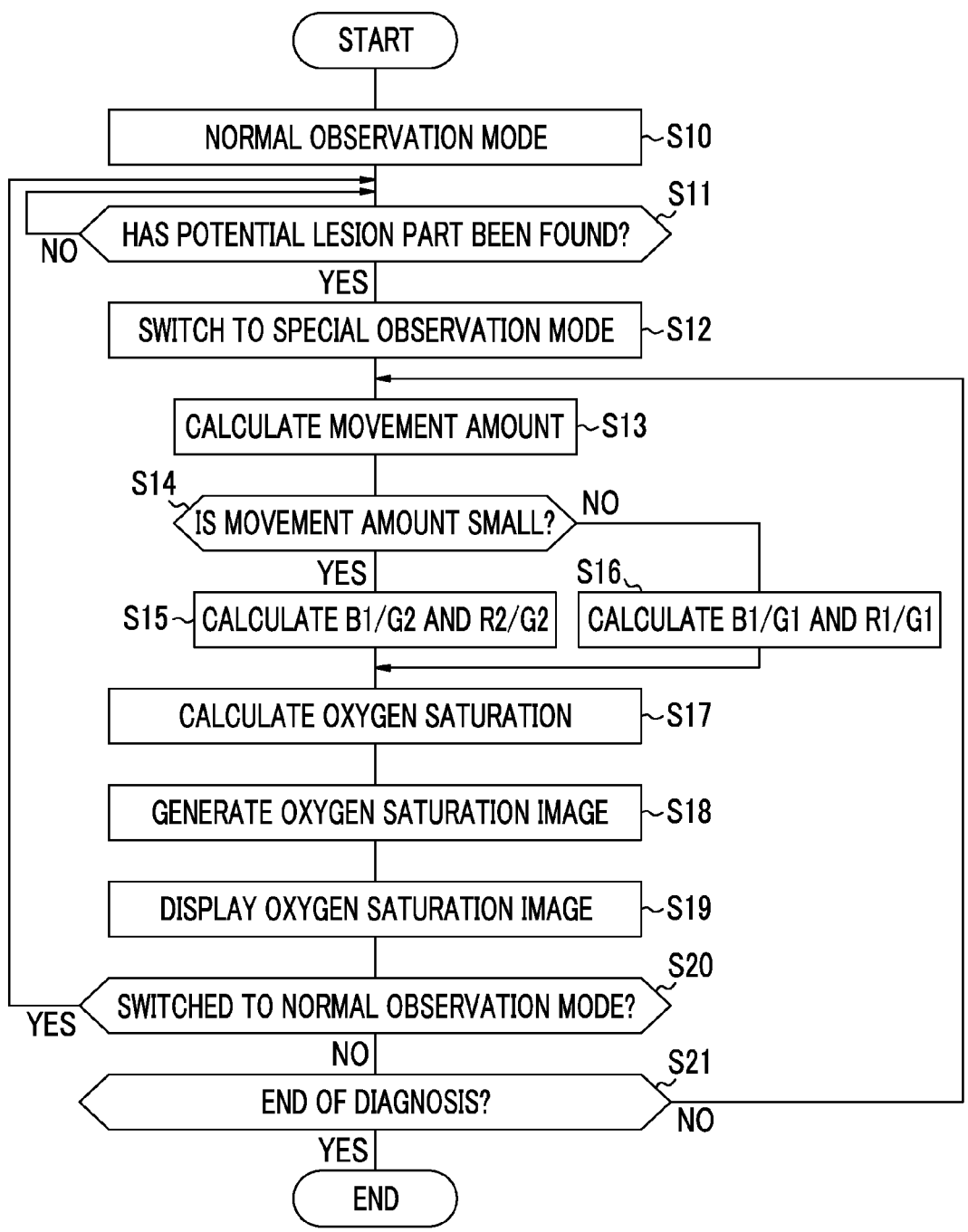
FIG. 12 is a flowchart showing the operation of the endoscope system.

Next, the flow of observation using the endoscope system 10 according to the present embodiment will be described with reference to the flowchart in FIG. 12. First, in the normal observation mode, screening is performed from the most distant view state (S10). In the normal observation mode, a normal observation image is displayed on the monitor 18. When a part that is likely to be a lesion (hereinafter, referred to as a potential lesion part), such as a brownish area or rubor, is found in this screening (S11), the mode selector SW 22b is operated for switching to the special observation mode (S12). Then, in the special observation mode, the potential lesion part is diagnosed.

In the special observation mode, the first and second white light beams are alternately emitted to the observation target in synchronization with the imaging frame of the sensor 48. Accordingly, the sensor 48 outputs the R1 image signal, the G1 image signal, and the B1 image signal in the first frame, and outputs the R2 image signal, the G2 image signal, and the B2 image signal in the second frame (imaging step (S12)). Then, in the processor device 16, when these imaging signals are received by the receiving unit 54 (receiving step (S12)), the movement amount calculation unit 65 calculates a signal ratio between the R1 image signal and the R2 image signal, among the image signals of two frames, for each pixel and calculates the average value as the movement amount (S13: movement amount calculation step).

The mode switching section 80 compares the movement amount with a threshold value (S14). When the movement amount is small and accordingly falls within the specific range determined by the threshold value, a mode to calculate the oxygen saturation is set as the first mode (S14:YES). On the other hand, when the movement amount is large and accordingly does not fall within the specific range determined by the threshold value, the mode to calculate the oxygen saturation is set to the second mode (S14:NO).

When the mode to calculate the oxygen saturation is set as the first mode, the signal ratio B1/G2 and the signal ratio R2/G2 are calculated by the signal ratio calculation section 81 (S15: signal ratio calculation step). However, when calculating the signal ratio B1/G2, a B1 image signal obtained by performing correction processing for removing the signal value based on the first fluorescence from a B1 image signal acquired through the image processing switching unit 60 is used. On the other hand, when the mode to calculate the oxygen saturation is set as the second mode, the signal ratio B1/G1 and the signal ratio R1/G1 are calculated by the signal ratio calculation section 81 (S16: signal ratio calculation step). However, when calculating the signal ratios B1/G1 and R1/G1, a B1 image signal obtained by performing correction processing for removing the signal value based on the first fluorescence from the B1 image signal acquired through the image processing switching unit 60 and a G1 image signal obtained by performing correction processing for removing the signal value based on the first laser light from the G1 image signal are used.

After the signal ratios are calculated according to the calculation mode as described above, the oxygen saturation calculation section 83 calculates the oxygen saturation for each pixel based on the calculated signal ratios (S17: oxygen saturation calculation step). After the oxygen saturation is calculated, an oxygen saturation image is generated by the image generation section 84 (S18). When the mode to calculate the oxygen saturation is set to the first mode, an oxygen saturation image is generated by multiplying the B2 image signal, the G2 image signal, and the R2 image signal by a gain according to the oxygen saturation calculated based on the signal ratio B1/G2 and the signal ratio R2/G2.

On the other hand, when the mode to calculate the oxygen saturation is set to the second mode, an oxygen saturation image is generated by multiplying the B1 image signal, the G1 image signal, and the R1 image signal by a gain according to the oxygen saturation calculated based on the signal ratios B1/G1 and the signal ratio R1/G1. Then, the generated oxygen saturation image is displayed on the monitor 18 (S19: display step). These operations are repeatedly performed until the switching to the normal observation mode (S20) or until the end of diagnosis (S21).

As described above, in the first mode set when the movement of the observation target is small, the oxygen saturation is calculated and the oxygen saturation image is generated using both of the first image signal acquired in the first frame and the second image signal acquired in the second frame. On the other hand, in the second mode set when the movement of the observation target is large, the oxygen saturation is calculated and the oxygen saturation image is generated using only the first image signal acquired in the first frame without using the second image signal acquired in the second frame. Then, switching between the first and second modes is automatically performed based on the movement amount.

In the first mode, it is possible to calculate a particularly accurate oxygen saturation, but image signals of two frames are required to calculate the oxygen saturation. For this reason, when there is a movement of the observation target, the calculation accuracy of the oxygen saturation is reduced. In the second mode, in order to increase the calculation accuracy of the oxygen saturation, it is necessary to calculate the signal ratios B1/G1 and R1/G1 after performing correction processing on two image signals of the B1 image signal and the G2 image signal. In the second mode, the calculation accuracy of the oxygen saturation is low compared with the first mode, but only the image signal of one frame is used. Accordingly, even if there is a movement of the observation target, the calculation accuracy of the oxygen saturation is hardly reduced. For this reason, in the endoscope system 10, the movement of the observation target is detected by calculating the movement amount of the observation target as described above, and switching between the first and second modes is automatically performed according to the magnitude of the movement of the observation target calculated as the movement amount.

Therefore, in the examination performed with a minimal change in the position or direction of the distal portion 24, that is, when there is almost no movement of the observation target, the first mode is automatically selected. As a result, it is possible to calculate and present a more accurate oxygen saturation than at the time of screening. In addition, at the time of screening performed while changing the position or direction of the distal portion 24, that is, when there is a large movement of the observation target, the second mode is automatically selected. As a result, it is possible to calculate and present the accurate degree of oxygen saturation without causing misdiagnosis. Needless to say, even when there is a movement of the observation target due to peristaltic movement or the like in the detailed examination, if the movement is large, switching to the second mode is automatically performed. As a result, the calculation and presentation of the accurate oxygen saturation are maintained. Even at the time of screening, if there is no movement of the observation target, switching to the first mode is automatically performed. As a result, it is possible to calculate and present the oxygen saturation that is more accurate than in the case where the second mode continues. That is, the endoscope system 10 can calculate and present the oxygen saturation that is as accurate as possible even if there is a movement of the observation target.

[Second Embodiment]

Figure 13:
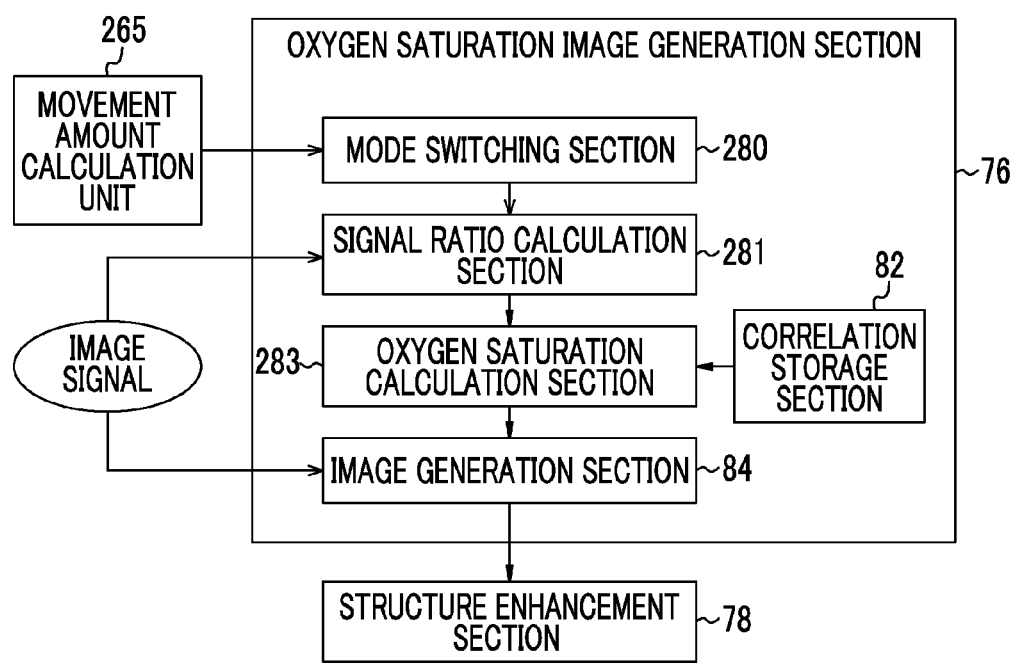
FIG. 13 is a block diagram showing a movement amount calculation unit and an oxygen saturation image generation section of a second embodiment.

An endoscope system according to a second embodiment is formed by replacing the movement amount calculation unit 65 and the mode switching section 80, the signal ratio calculation section 81, and the oxygen saturation calculation section 83 of the oxygen saturation image generation section 76 in the first embodiment with a movement amount calculation unit 265, a mode switching section 280, a signal ratio calculation section 281, and an oxygen saturation calculation section 283 shown in FIG. 13. Other configurations are the same as the endoscope system 10 according to the first embodiment.

Figure 14:
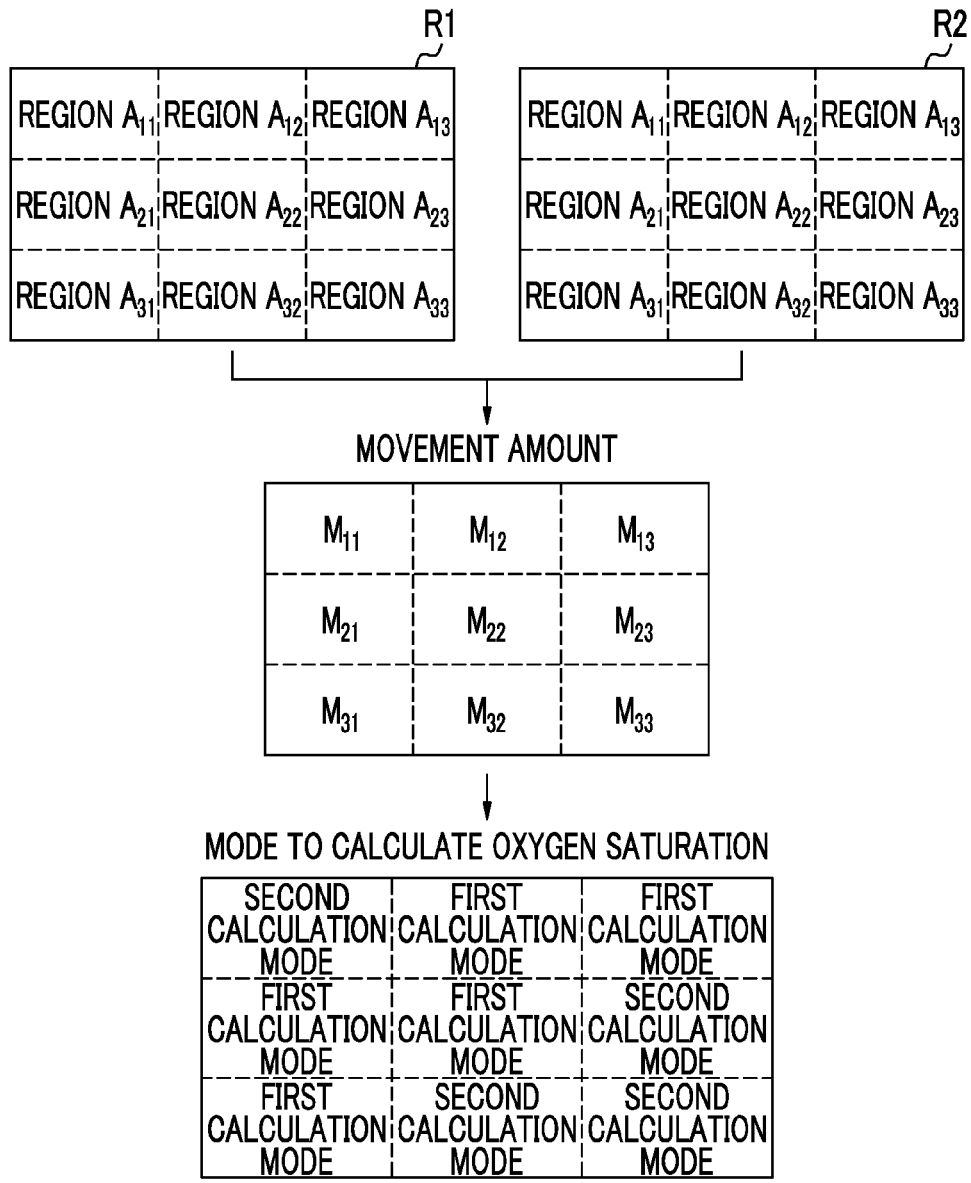
FIG. 14 is a diagram for explaining the switching between modes to calculate the oxygen saturation for a plurality of regions.

The movement amount calculation unit 265 is the same as the movement amount calculation unit 65 of the first embodiment in that an image signal is acquired from the image processing switching unit 60 and the movement amount is calculated using the acquired image signal when the observation mode selector SW 22b is set to the special observation mode and the same method is used. However, the movement amount calculation unit 265 divides the imaging region expressed by the first image signal (or the second image signal) into a plurality of regions, and calculates the movement amount in each region. For example, as shown in FIG. 14, the movement amount calculation unit 265 divides the imaging region expressed by the R1 image signal (reference numeral R1) and the R2 image signal (reference numeral R2) into "3×3" regions $A_{ij}$ (i=1 to 3, j=1 to 3), and calculates a movement amount $M_{ij}$ in each region $A_{ij}$.

In addition, the mode switching section 280 compares the movement amount in each region $A_{ij}$ with a threshold value, and inputs to the signal ratio calculation section 281 a mode setting signal for switching the mode to calculate the oxygen saturation for each region $A_{ij}$ according to the result. The mode setting signal designates the correspondence between each region $A_{ij}$ and the setting of a mode to calculate the oxygen saturation. For example, as shown in FIG. 14, when the movement amount $M_{22}$ of the central region $A_{22}$ falls within the specific range determined by the threshold value, the mode to calculate the oxygen saturation of the region $A_{22}$ is set to the first mode. As in the upper left region $A_{11}$, when the movement amount $M_{11}$ does not fall within the specific range determined by the threshold value, the mode to calculate the oxygen saturation of the region $A_{11}$ is set to the second mode. The threshold value used by the mode switching section 280 is the same as that used in the mode switching section 80 of the first embodiment.

The signal ratio calculation section 281 calculates a signal ratio used in the oxygen saturation calculation section 283 according to the mode setting signal input from the mode switching section 80. The signal ratio calculation method or the like based on each calculation mode is the same as that used by the signal ratio calculation section 81 of the first embodiment. However, the signal ratio calculation section 281 calculates a signal ratio according to the calculation mode designated by the mode setting signal for each region described above. Accordingly, the signal ratio B1/G2 and the signal ratio R2/G2 are calculated in a region set to the first mode, and the signal ratio B1/G1 and the signal ratio R1/G1 are calculated in a region set to the second mode.

The oxygen saturation calculation section 283 calculates the oxygen saturation based on the signal ratio of each region input from the signal ratio calculation section 281, and the correlation stored in the correlation storage section 82. For this reason, the oxygen saturation is calculated using the signal ratio B1/G2 and the signal ratio R2/G2 in the region set to the first mode, and the oxygen saturation is calculated using the signal ratio B1/G1 and the signal ratio R1/G1 in the region set to the second mode.

As described above, by dividing the image signal into a plurality of regions $A_{ij}$, calculating the movement amount $M_{ij}$ in each region $A_{ij}$, setting the mode to calculate the oxygen saturation for each region $A_{ij}$ based on the magnitude of the movement amount $M_{ij}$, it is possible to calculate and present the accurate oxygen saturation even if there is a partial movement of the observation target. For example, the calculation and presentation of the particularly accurate oxygen saturation are maintained by the first mode in a region where there is no movement of the observation target, and the accuracy of the oxygen saturation is ensured by the second mode in a region where there is a movement of the observation target.

Although the imaging signal is divided into the "3×3" regions $A_{ij}$ in FIG. 14, the region division method or the number of divided regions is arbitrary, and the number of regions in the horizontal and vertical directions of the image signal may be different. For example, the imaging signal may be divided into the "4×5" regions. In addition, the shape of each region may not be a square shown in FIG. 14. For example, the image signal may be divided into a plurality of concentric circular regions.

In addition, the smallest unit of a region obtained by dividing the image signal is one pixel. In this case, each pixel is the above-described region, and the mode to calculate the oxygen saturation is changed by calculating the movement amount for each pixel. Thus, by calculating the movement amount and changing the mode to calculate the oxygen saturation for each pixel, a boundary of regions having different modes to calculate the oxygen saturation in the oxygen saturation image is hardly noticeable especially.

[Third Embodiment]

Figure 15:
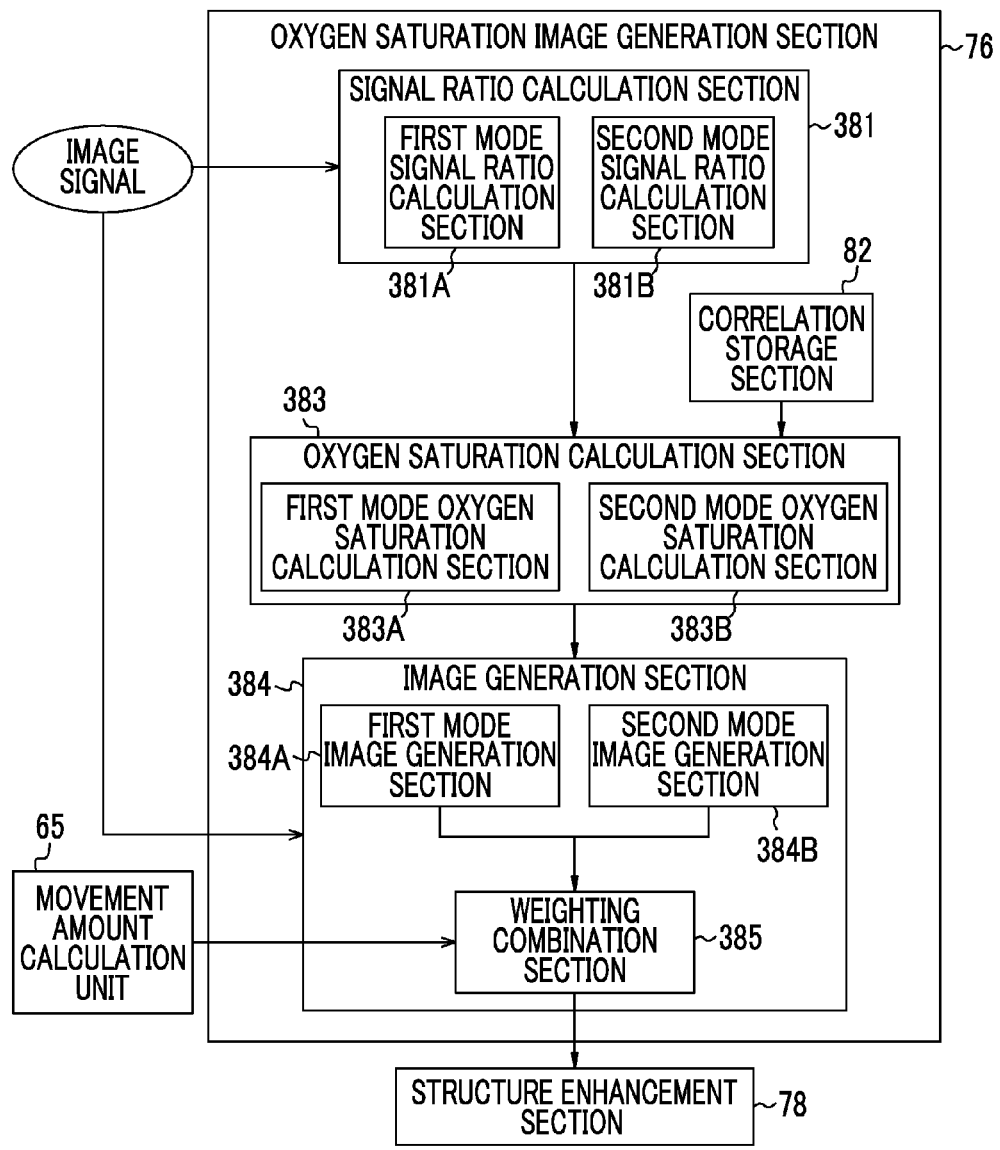
FIG. 15 is a block diagram showing an oxygen saturation image generation section of a third embodiment.

An endoscope system according to a third embodiment is formed by replacing the signal ratio calculation section 81, the oxygen saturation calculation section 83, and the image generation section 84 of the first embodiment with a signal ratio calculation section 381, an oxygen saturation calculation section 383, and an image generation section 384 shown in FIG. 15. In the endoscope system according to the third embodiment, the mode switching section 80 is not provided, and the movement amount calculated by the movement amount calculation unit 65 is input to the image generation section 384. Other configurations are the same as that of the endoscope system 10 according to the first embodiment.

The signal ratio calculation section 381 includes a first mode signal ratio calculation section 381A and a second mode signal ratio calculation section 381B. The first mode signal ratio calculation section 381A calculates the signal ratios B1/G2 and R2/G2 in the first mode, and the second mode signal ratio calculation section 381B calculates the signal ratios B1/G1 and R1/G1 in the second mode. That is, the signal ratio calculation section 381 calculates both of the signal ratios B1/G2 and R2/G2 for the first mode and the signal ratios B1/G1 and R1/G1 for the second mode at all times without depending on the movement amount. The method used when each of the first mode signal ratio calculation section 381A and the second mode signal ratio calculation section 381B calculates the above signal ratio is the same as the method used by the signal ratio calculation section 81 of the first embodiment.

The oxygen saturation calculation section 383 includes a first mode oxygen saturation calculation section 383A and a second mode oxygen saturation calculation section 383B. The first mode oxygen saturation calculation section 383A calculates the oxygen saturation of each pixel based on the signal ratios B1/G2 and R2/G2 calculated by the first mode signal ratio calculation section 381A and the correlation stored in the correlation storage section 82. In addition, the second mode oxygen saturation calculation section 383B calculates the oxygen saturation of each pixel based on the signal ratios B1/G1 and R1/G1 calculated by the second mode signal ratio calculation section 381B and the correlation stored in the correlation storage section 82. That is, the oxygen saturation calculation section 383 calculates the oxygen saturation in the first mode and calculates the oxygen saturation in the second mode at all times without depending on the movement amount.

The image generation section 384 includes a first mode image generation section 384A, a second mode image generation section 384B, and a weighting combination section 385. The first mode image generation section 384A generates an oxygen saturation image using the oxygen saturation calculated by the first mode oxygen saturation calculation section 383A, the B2 image signal, the G2 image signal, and the R2 image signal. The oxygen saturation image generated by the first mode image generation section 384A (hereinafter, referred to as a first mode image) is an oxygen saturation image calculated when the first mode is set in the first embodiment. In addition, the second mode image generation section 384B generates an oxygen saturation image using the oxygen saturation generated by the second mode oxygen saturation calculation section 383B, the B1 image signal, the G1 image signal, and the R1 image signal. The oxygen saturation image calculated by the second mode image generation section 384B (hereinafter, referred to as a second mode image) is an oxygen saturation image calculated when the second mode is set in the first embodiment. Accordingly, the image generation section 384 generates the first mode image and the second mode image at all times without depending on the movement amount.

Figure 16:
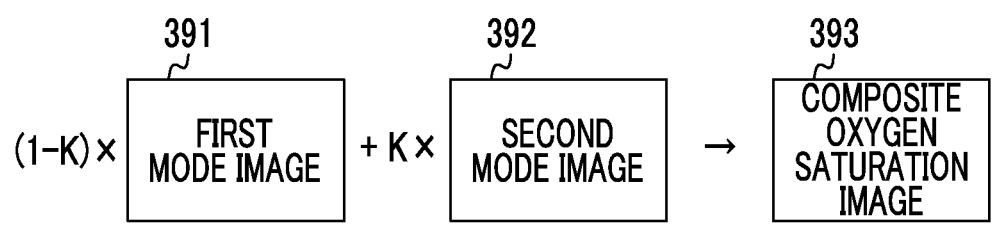
FIG. 16 is a diagram for explaining the generation of a composite oxygen saturation image based on the combination of weighted first and second mode images.

The weighting combination section 385 generates a composite oxygen saturation image by combining the first and second mode images. This combination is performed using a weighting coefficient K based on the movement amount. Specifically, first, the weighting combination section 385 calculates the weighting coefficient K based on the movement amount input from the movement amount calculation unit 65. The weighting coefficient K is calculated as a value of "0" to "1". The weighting coefficient K is "0" when the movement amount is "1" (value of R2/R1 when there is no movement of the observation target) and "1" when the movement amount is the same value as the threshold value set in advance. When the movement amount is a value of "1" to threshold value, the weighting coefficient K is set to a value in the range of "0" to "1" in proportion to the magnitude of the movement amount. In addition, when the movement amount exceeds the threshold value, the weighting coefficient K is set to "1". After calculating the weighting coefficient K, a composite oxygen saturation image 393 is generated by multiplying a first mode image 391 by "1−K" and multiplying a second mode image 392 by "K" and adding the signal values for each pixel as shown in FIG. 16. The composite oxygen saturation image 393 generated as described above is output to the structure enhancement section 78 as an oxygen saturation image for display, and is displayed on the monitor 18.

Figure 17:
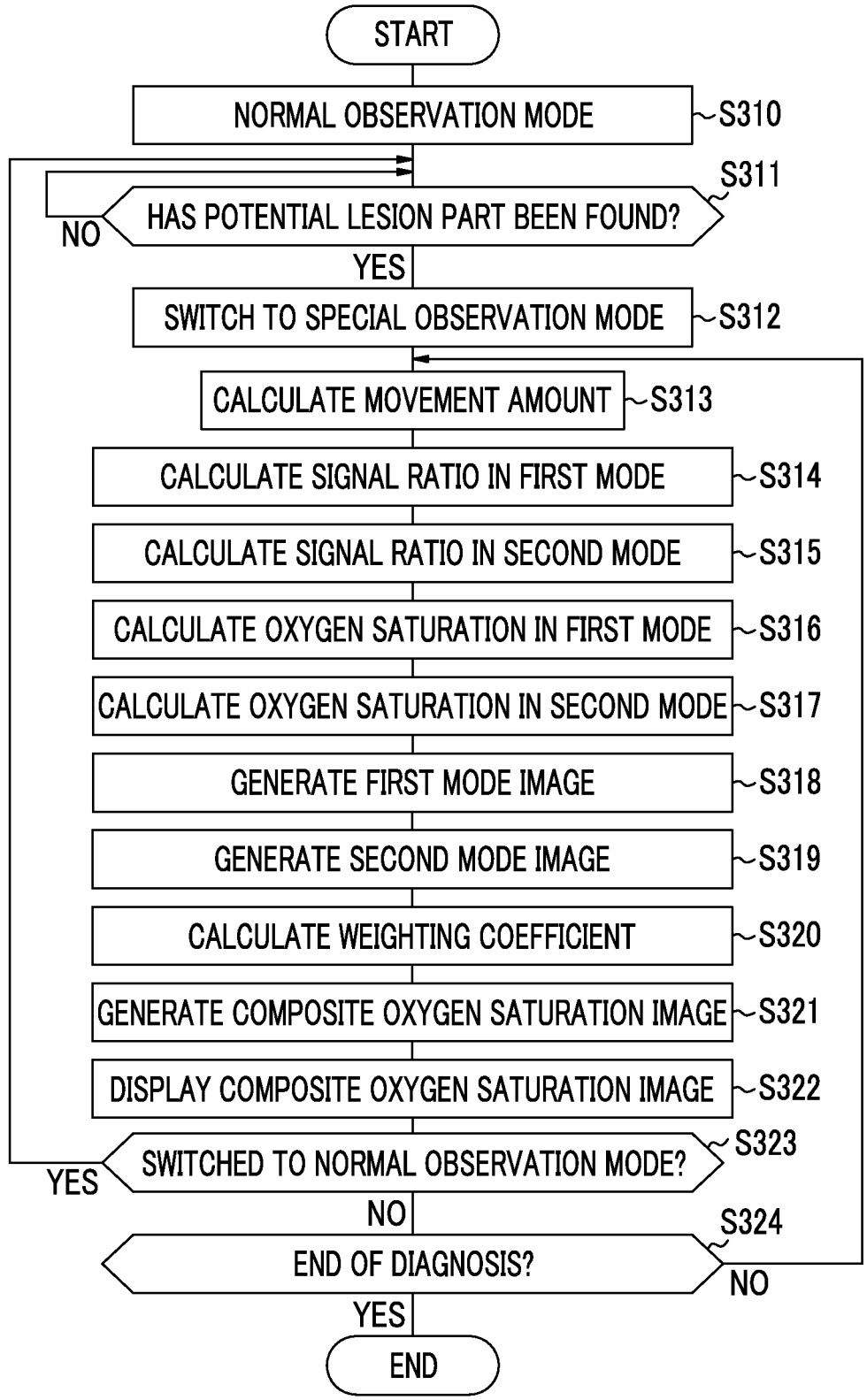
FIG. 17 is a flowchart showing the operation in the third embodiment.

Also when generating the composite oxygen saturation image 393 as described above, in the same manner as in the first embodiment, screening is performed in the normal observation mode first (S310), as shown in FIG. 17. When a potential lesion part is found (S311), switching to the special observation mode is performed by operating the mode selector SW 22b (S312), and the potential lesion part is diagnosed in the special observation mode.

In the special observation mode, the first and second white light beams are alternately emitted to the observation target in synchronization with the imaging frame of the sensor 48. Therefore, since the sensor 48 outputs the R1 image signal, the G1 image signal, and the B1 image signal in the first frame, and outputs the R2 image signal, the G2 image signal, and the B2 image signal in the second frame, the movement amount is calculated by the movement amount calculation unit 65 as in the first embodiment (S313).

Thereafter, in the first embodiment, the calculation of the oxygen saturation and the generation of the oxygen saturation image are performed by performing switching between the first and second modes based on the movement amount. In the present embodiment, however, without depending on the magnitude of the movement amount or the like, the first mode signal ratios B1/G2 and R2/G2 are calculated (S314: first signal ratio calculation step) and the second mode signal ratios B1/G1 and R1/G1 are calculated (S315: second signal ratio calculation step). Then, based on the signal ratios for first and second modes, the oxygen saturation in the first mode and the oxygen saturation in the second mode are calculated (S316: first oxygen saturation calculation step and S317: second oxygen saturation calculation step).

After the oxygen saturation in each of the first and second calculation modes is calculated, the first mode image 391 is generated using the first mode oxygen saturation (S318: first mode image generation step), and the second mode image 392 is generated using the second mode oxygen saturation (S319: second mode image generation step). In addition, the weighting coefficient K corresponding to the movement amount calculated in step 313 is calculated by the weighting combination section 385 (S320: weighting coefficient calculation step), and the first mode image 391 and the second mode image 392 are combined at the ratio corresponding to the weighting coefficient K to generate the composite oxygen saturation image 393 (S321: combination step). In the present embodiment, the composite oxygen saturation image 393 generated as described above is displayed on the monitor 18 after structure enhancement or the like (S322: display step). These operations are repeatedly performed until the switching to the normal observation mode (S323) or until the end of diagnosis (S324) as in the first embodiment.

When the composite oxygen saturation image 393 for display is generated by generating both of the first mode image 391 and the second mode image 392 at all times and combining the first mode image 391 and the second mode image 392 by giving a weighting thereto with the weighting coefficient K based on the movement amount, the ratio of the second mode image 392 in the composite oxygen saturation image 393 is large if the movement of the observation target is large, and the ratio of the first mode image 391 in the composite oxygen saturation image 393 is large if the movement of the observation target is small. Needless to say, the composite oxygen saturation image 393 becomes the first mode image 391 itself if the movement of the observation target is small, and the composite oxygen saturation image 393 becomes the second mode image 392 itself if the movement of the observation target is large. When the magnitude of the movement of the observation target is an intermediate level of the above, an image of the oxygen saturation calculated in the first or second mode that has higher reliability strongly appears in the composite oxygen saturation image.

According to the present embodiment, it is possible to calculate and present the accurate oxygen saturation without a doctor or the like paying attention to the switching between the first and second modes. In addition, compared with a case where the mode to calculate the oxygen saturation is switched for each region as in the second embodiment, the composite oxygen saturation image 393 of the present embodiment has good visibility because there is no boundary between adjacent regions having different modes to calculate the oxygen saturation.

In addition, the image signal may be divided into a plurality of regions as in the second embodiment, and a composite image corresponding to the composite oxygen saturation image 393 may be generated in each of the regions as described above. Thus, if the present embodiment is combined with the second embodiment, the boundary of regions is not noticeable. As a result, it is possible to provide an oxygen saturation image with high visibility.

[Fourth Embodiment]

Figure 18:
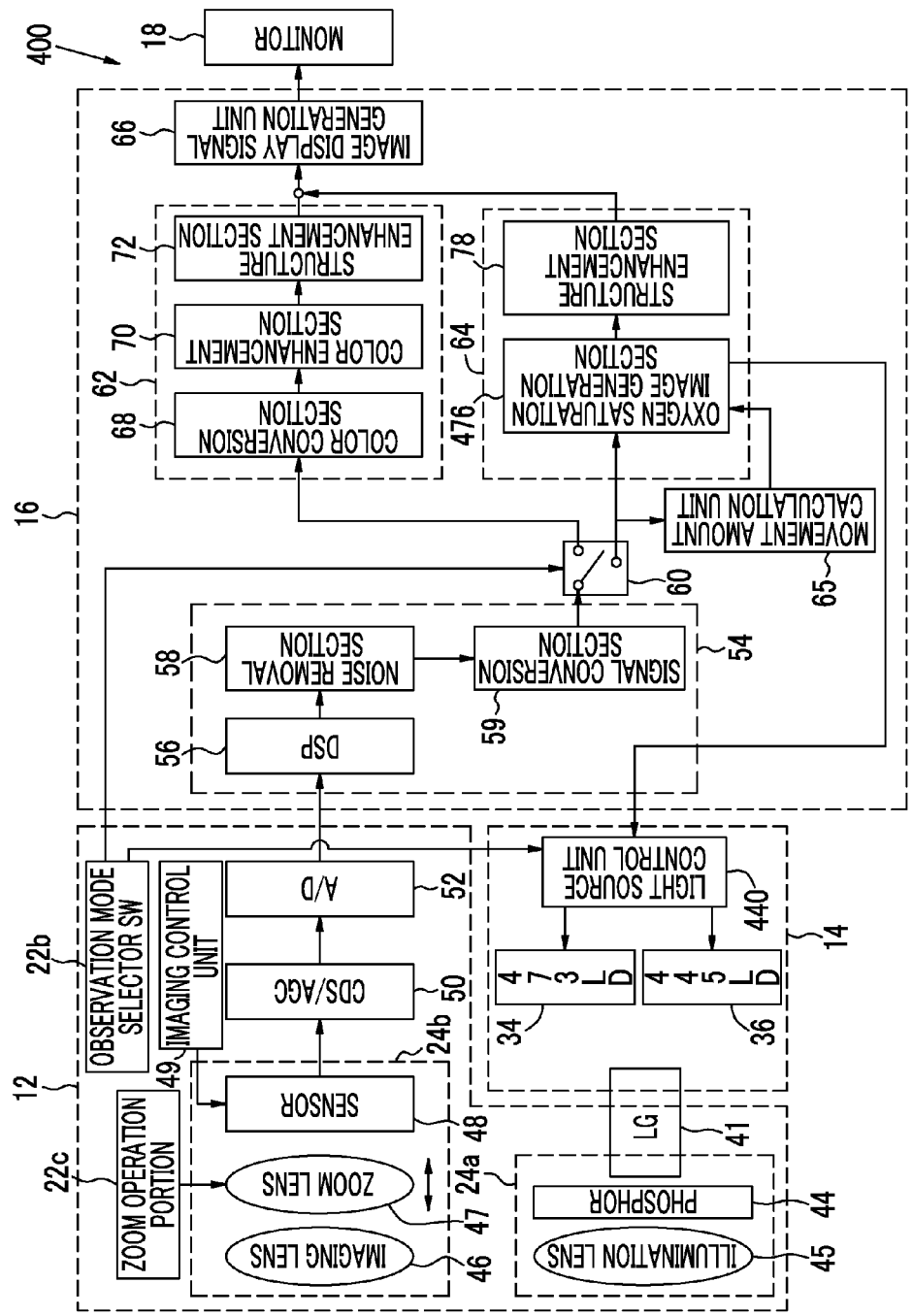
FIG. 18 is a block diagram of an endoscope system according to a fourth embodiment.

As shown in FIG. 18, an endoscope system 400 according to a fourth embodiment includes an movement amount calculation unit 465, an oxygen saturation image generation section 476, and a light source control unit 440 that are different from those in the first embodiment. Other configurations are the same as that of the endoscope system 10 according to the first embodiment.

The movement amount calculation unit 465 stores at least one color of the first image signal acquired in the past frame, extracts a corresponding feature point from the past frame image and the latest first image signal acquired through the image processing switching unit 60, calculates a motion vector indicating the direction and magnitude of the movement of the observation target from the positional relationship, and calculates the magnitude as the movement amount. When extracting a plurality of feature points, for example, the average value of the magnitude of the motion vector calculated from the plurality of feature points is calculated as the movement amount.

The oxygen saturation image generation section 476 performs the calculation of the oxygen saturation and the generation of the oxygen saturation image in the same manner as the oxygen saturation image generation section 76 of the first embodiment, but inputs the mode setting signal output from the mode switching section 80 not only to the signal ratio calculation section 81 but also to the light source control unit 440.

Figure 19:
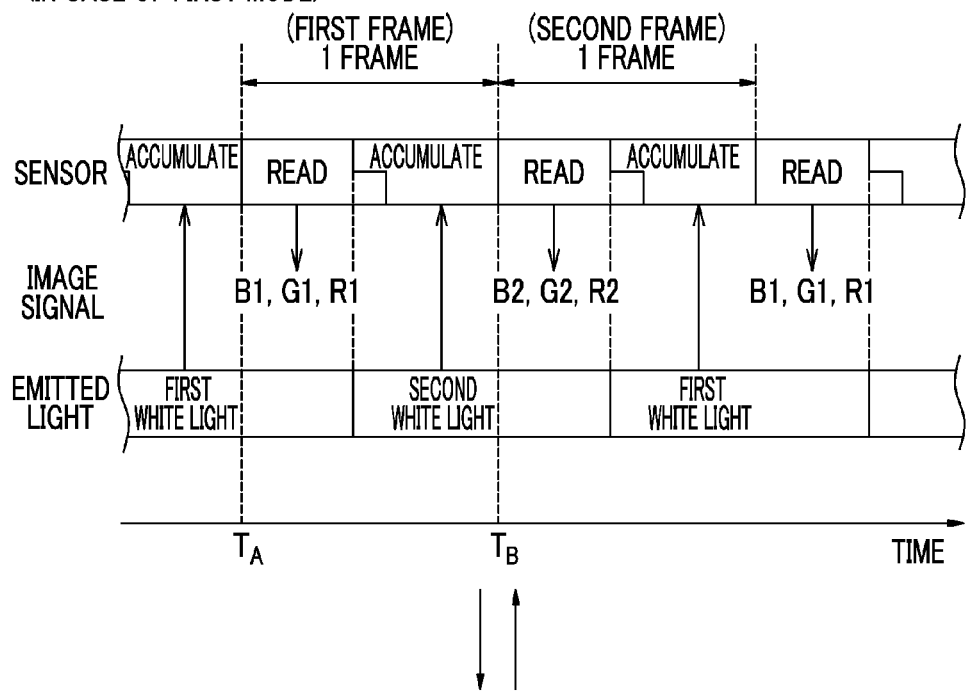
FIG. 19 is an explanatory diagram showing a control state in the fourth embodiment.
Figure 19:
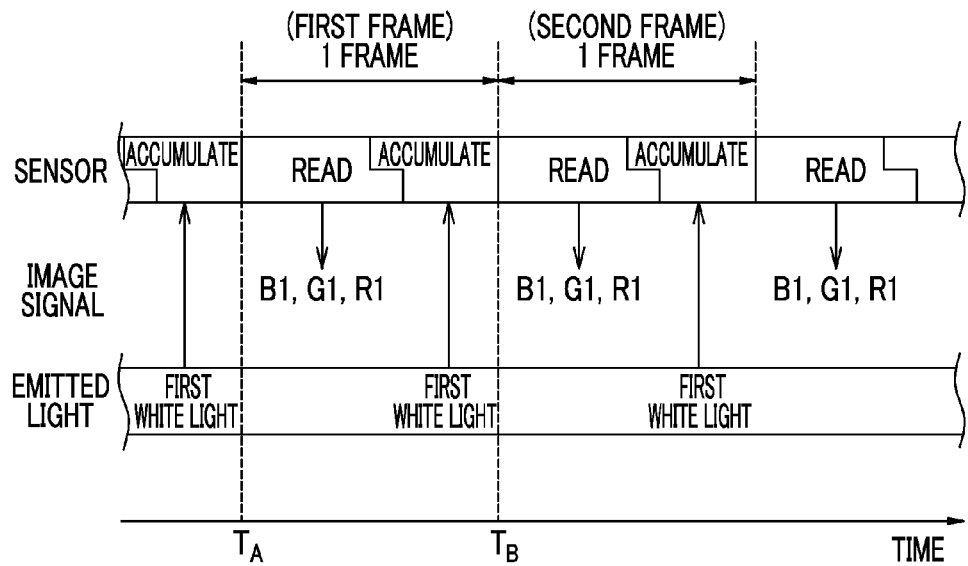

As shown in FIG. 19, when the mode setting signal input from the oxygen saturation image generation section 76 indicates the first mode, the light source control unit 440 turns on the first blue laser light source (473 LD) 34 and the second blue laser light source (445 LD) 36 alternately in synchronization with the imaging frame as in the first embodiment. On the other hand, when the input mode setting signal indicates the second mode, even in the special observation mode, the light source control unit 440 turns on only the first blue laser light source (473 LD) 34 continuously until the mode setting signal for setting the first mode is received. In this case, in both of the first and second frames, the first white light is emitted to the observation target, and the sensor 48 outputs the B1 image signal, the G1 image signal, and the R1 image signal. Therefore, the oxygen saturation image generation section 476 performs the calculation of the oxygen saturation and the generation of the oxygen saturation image in the first mode for each frame.

According to the control described above, while the observation target is moving largely (fast), imaging and the frame rate to display the oxygen saturation image are automatically improved while calculating and presenting the accurate oxygen saturation. As a result, the visibility of the observation target is improved.

Also in the first to third embodiments, the movement amount may be calculated by using the same method as that used by the movement amount calculation unit 465 of the present embodiment.

[Fifth Embodiment]

Figure 20:
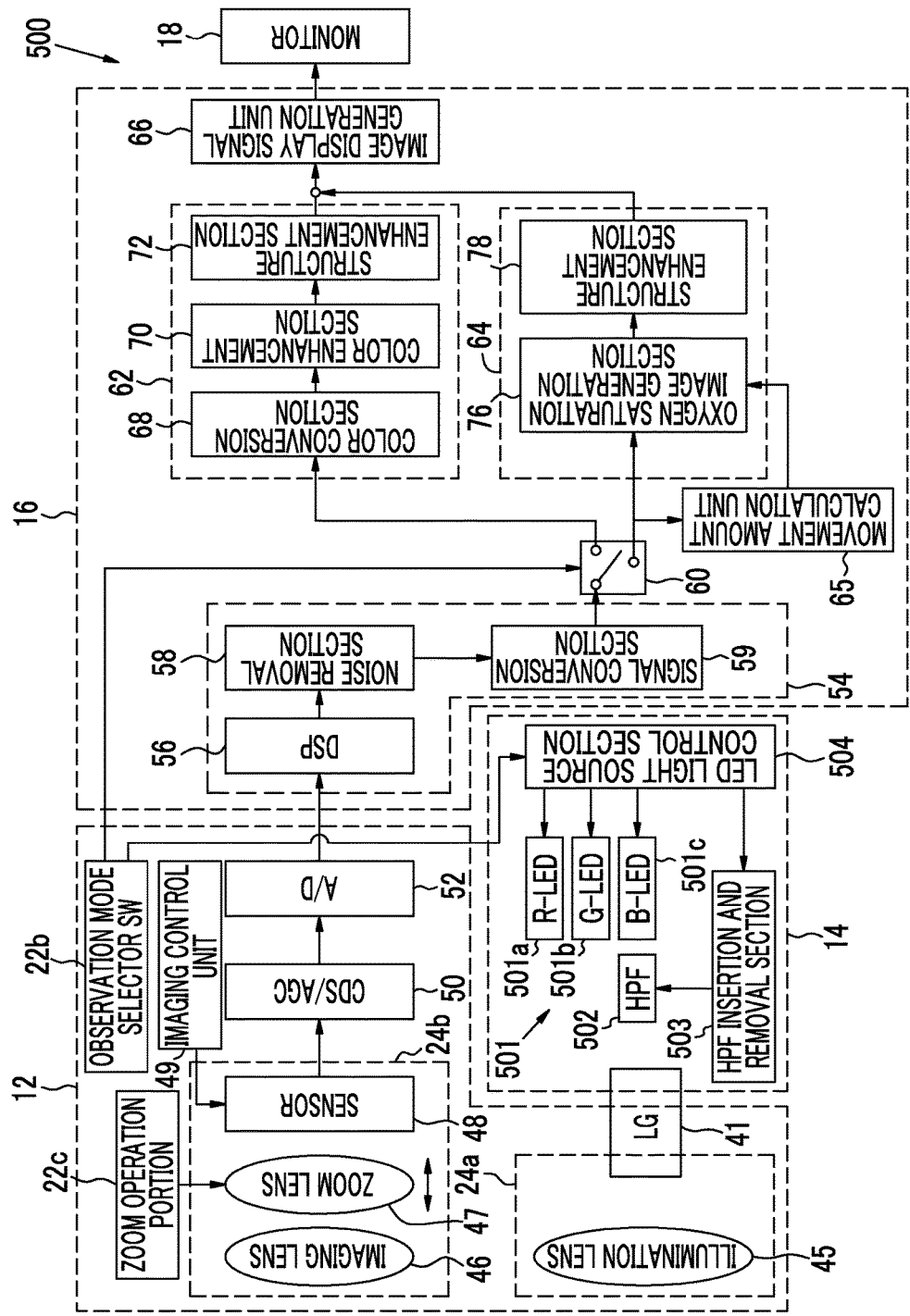
FIG. 20 is a block diagram of an endoscope system according to a fifth embodiment.

As shown in FIG. 20, in a light source device 14 of an endoscope system 700, a light emitting diode (LED) light source unit 501 and an LED light source control section 504 are provided instead of the first and second blue laser light sources 34 and 36 and the light source control unit 40. In addition, the phosphor 44 is not provided in an illumination optical system 24a of an endoscope system 500. Other than these, the endoscope system 500 is the same as the endoscope system 10 according to the first embodiment.

Figure 21:
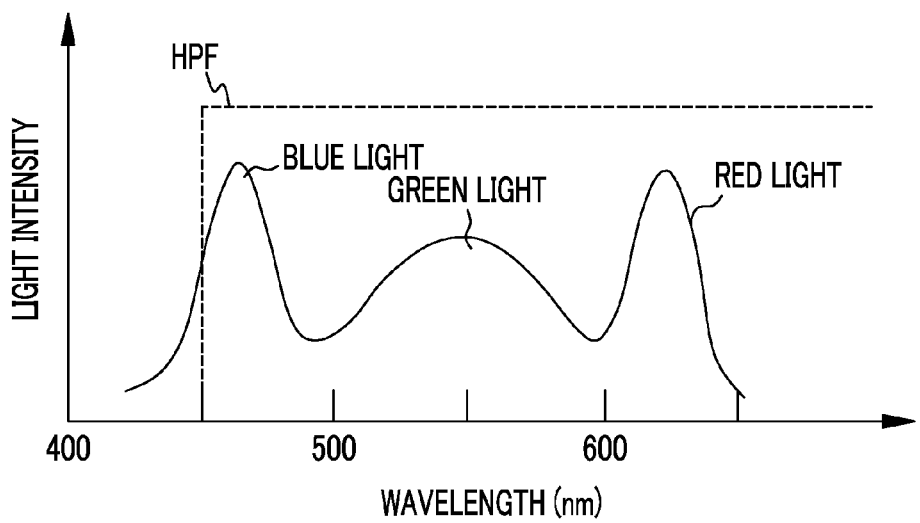
FIG. 21 is a graph showing the light emission band of an LED and the characteristics of an HPF.

The LED light source unit 501 includes an R-LED 501a, a G-LED 501b, and a B-LED 501c as light sources for emitting light limited to a specific wavelength band. As shown in FIG. 21, the R-LED 501a emits red band light (hereinafter, simply referred to as red light) having a wavelength of about 600 nm to 650 nm, for example. The center wavelength of the red light is about 620 nm to 630 nm. The G-LED 501b emits green band light (hereinafter, simply referred to as green light) having a wavelength of about 500 nm to 600 nm that is expressed by a normal distribution. The B-LED 501c emits blue band light (hereinafter, simply referred to as blue light) having a center wavelength of 445 nm to 460 nm.

In addition, the LED light source unit 501 includes a high pass filter (HPF) 502 that is removably inserted on the optical path of the blue light emitted from the B-LED 501c. The high pass filter 502 cuts the blue light having a wavelength in a wavelength band of about 450 nm or less, and allows light having a wavelength in a wavelength band higher than about 450 nm to be transmitted therethrough.

The cutoff wavelength (about 450 nm) of the high pass filter 502 is a wavelength at which the light absorption coefficient of oxygenated hemoglobin and the light absorption coefficient of reduced hemoglobin are almost equal (refer to FIG. 10), and the light absorption coefficient of oxygenated hemoglobin and the light absorption coefficient of reduced hemoglobin are reversed in the order of magnitude with the cutoff wavelength as a boundary. In the present embodiment, the correlation stored in the correlation storage section 82 is that the light absorption coefficient of oxygenated hemoglobin is larger than the light absorption coefficient of reduced hemoglobin. Accordingly, a signal based on the wavelength band equal to or lower than the cutoff wavelength is a cause by which incorrect oxygen saturation is calculated. Therefore, by preventing light having a wavelength in a wavelength band equal to or lower than the cutoff wavelength from being emitted to the observation target using the high pass filter 502 when acquiring at least the B1 image signal for calculating the oxygen saturation, the calculation accuracy of the oxygen saturation is improved.

Accordingly, the high pass filter 502 is inserted at the insertion position before the B-LED 501c in the special observation mode, and is retracted to the retraction position in the normal observation mode. The insertion and removal of the high pass filter 502 is performed by an HPF insertion and removal section 503 under the control of the LED light source control section 504.

Figure 22:
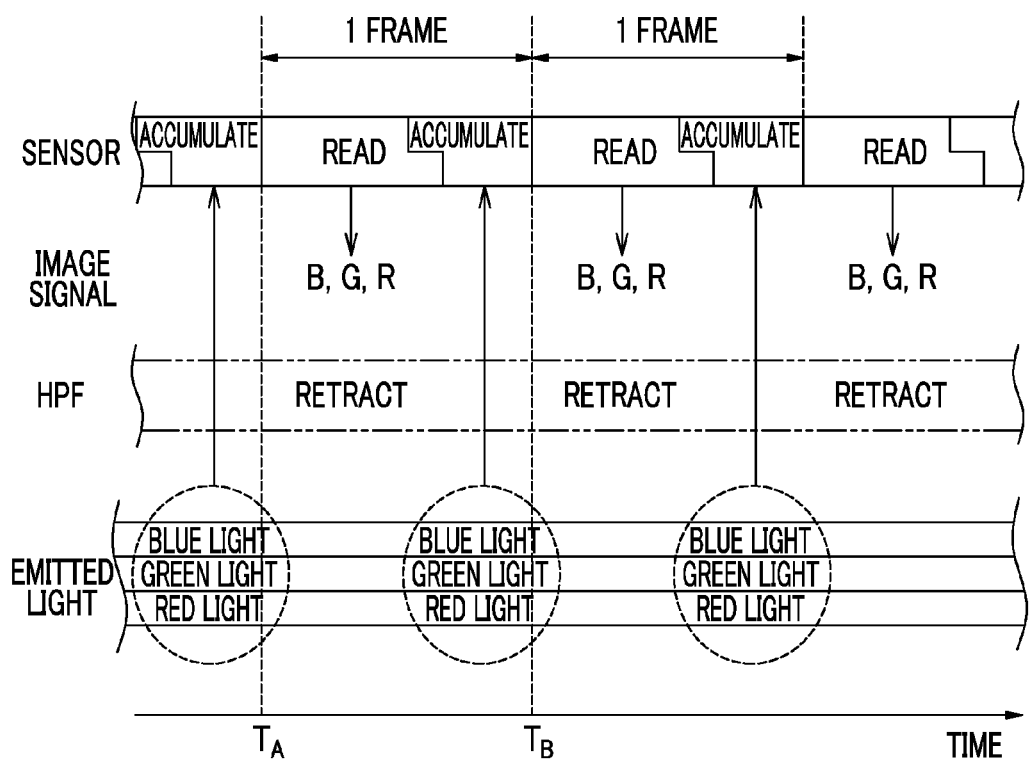
FIG. 22 is an explanatory diagram showing imaging control in the normal observation mode in the fifth embodiment.

The LED light source control section 504 controls ON/OFF of the LEDs 501a to 501c of the LED light source unit 501 and the insertion and removal of the high pass filter 502. Specifically, as shown in FIG. 22, in the normal observation mode, the LED light source control section 504 turns on all of the LEDs 501a to 501c and retracts the high pass filter 502 from the optical path of the B-LED 501c. Accordingly, white light in which blue light, green light, and red light are superimposed are emitted to the observation target, and the sensor 48 images the observation target with reflected light of the white light and outputs an image signal of each color of B, and R.

Figure 23:
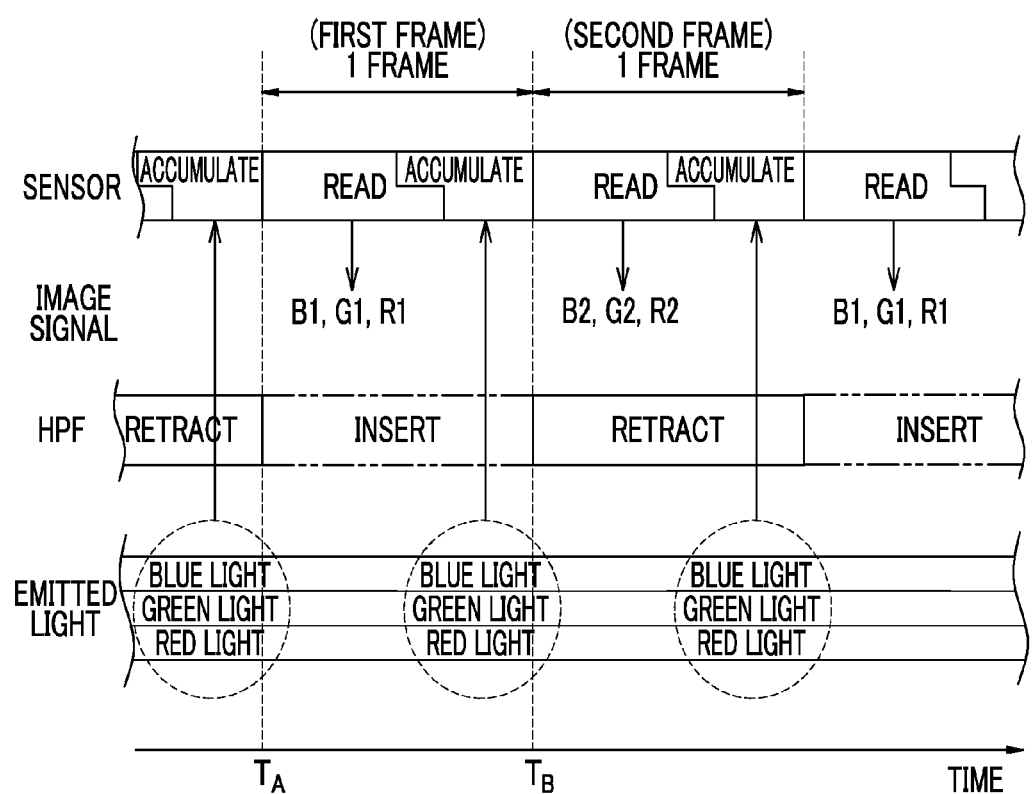
FIG. 23 is an explanatory view showing imaging control in the special observation mode in the fifth embodiment.

On the other hand, as shown in FIG. 23, in the special observation mode, the LED light source control section 504 inserts or retracts the high pass filter 502 for each frame in a state where all of the LEDs 501a to 501c are turned on. Accordingly, first mixed color light of blue light, green light, and red light when light having a wavelength in a wavelength band of 450 nm or less is cut off and second mixed color light of blue light, green light, and red light when light having a wavelength in a wavelength band of 450 nm or less is not cut off are alternately emitted to the observation target. The first mixed color light corresponds to the first white light in the first embodiment, and the second mixed color light corresponds to the second white light in the first embodiment.

Then, in the imaging control unit 49, a signal charge obtained by imaging the observation target under the first mixed color light is read in a reading period of the first frame, and the B1 image signal, the G1 image signal, and the R1 image signal are output. In addition, a signal charge obtained by imaging the observation target under the second mixed color light is read in a reading period of the second frame, and the B2 image signal, the G2 image signal, and the R2 image signal are output. Subsequent processing can be performed in the same manner as in the endoscope system 10.

In addition, the first and second mixed color light beams are first and second illumination light beams having different emission spectrums, and the R-LED 501a, the G-LED 501b, the B-LED 501c, and the high pass filter 502 form a light source that emits the first and second illumination light beams having different emission spectrums to the observation target.

[Reference Examples]

Figure 24:
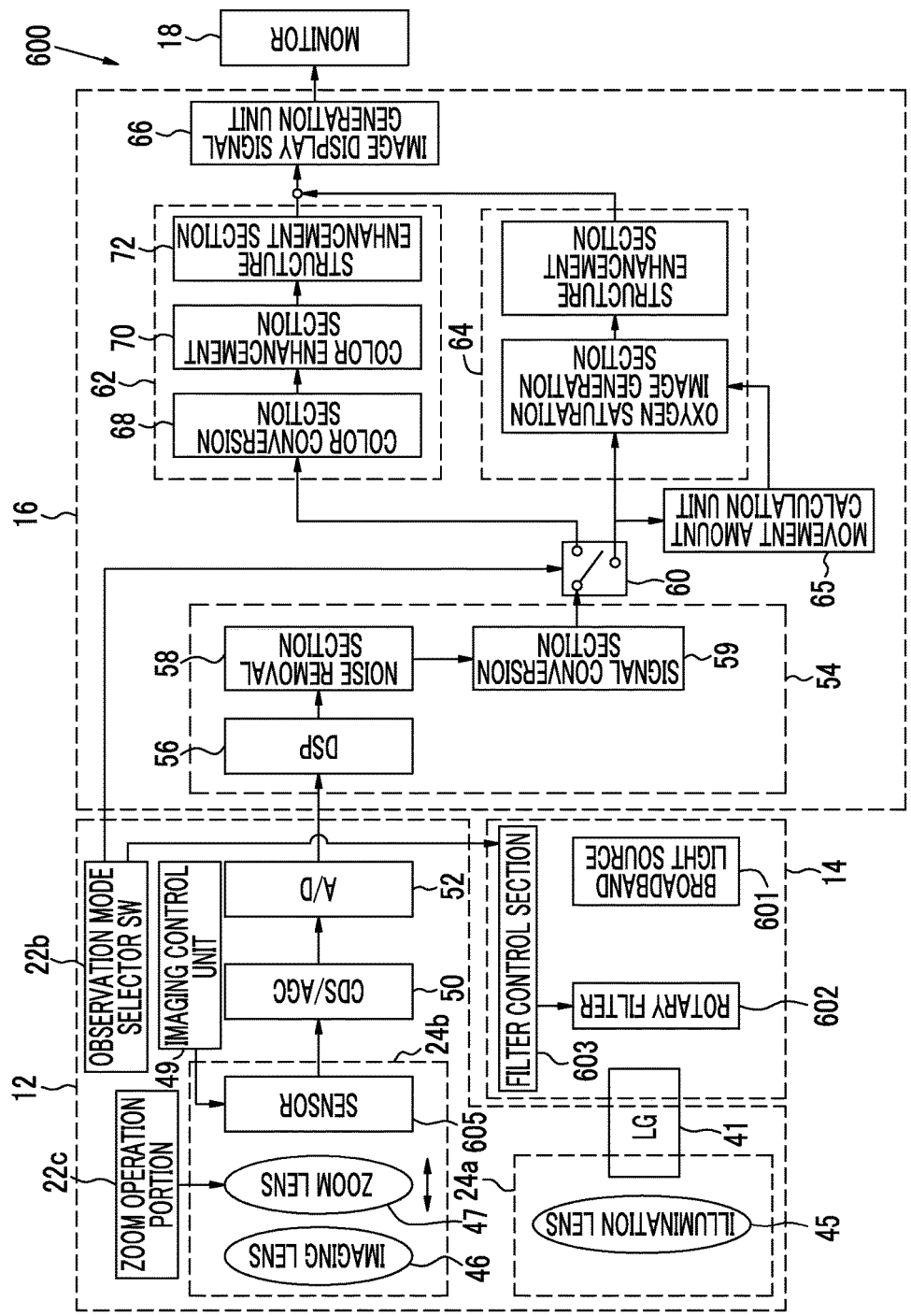
FIG. 24 is a block diagram of an endoscope system in a reference example.

As shown in FIG. 24, in a light source device 14 of an endoscope system 600, a broadband light source 601, a rotary filter 602, and a rotary filter control section 603 are provided instead of the first and second blue laser light sources 34 and 36 and the light source control unit 40. A sensor 605 of the endoscope system 600 is a monochrome imaging device in which no color filter is provided. Therefore, the DSP 56 does not perform processing specific to the color imaging device, such as demosaic processing. Other than these, the endoscope system 600 is the same as the endoscope system 10 according to the first embodiment.

The broadband light source 601 is, for example, a xenon lamp or a white LED, and emits white light having a wavelength in a wavelength band ranging from blue to red. The rotary filter 602 includes a normal observation mode filter 610 and a special observation mode filter 611 (refer to FIG. 25), and can move in a radial direction between a first position for normal observation mode to place a normal observation mode filter 610 on the optical path, in which the white light emitted from the broadband light source 601 is incident on the light guide 41, and a second position for special observation mode to place a special observation mode filter 611 on the optical path. The movement of the rotary filter 602 to the first and second positions is controlled by the rotary filter control section 603 according to the selected observation mode. In addition, the rotary filter 602 rotates according to the imaging frame of the sensor 605 while being placed at the first or second position. The rotation speed of the rotary filter 602 is controlled by the rotary filter control section 603 according to the selected observation mode.

Figure 25:
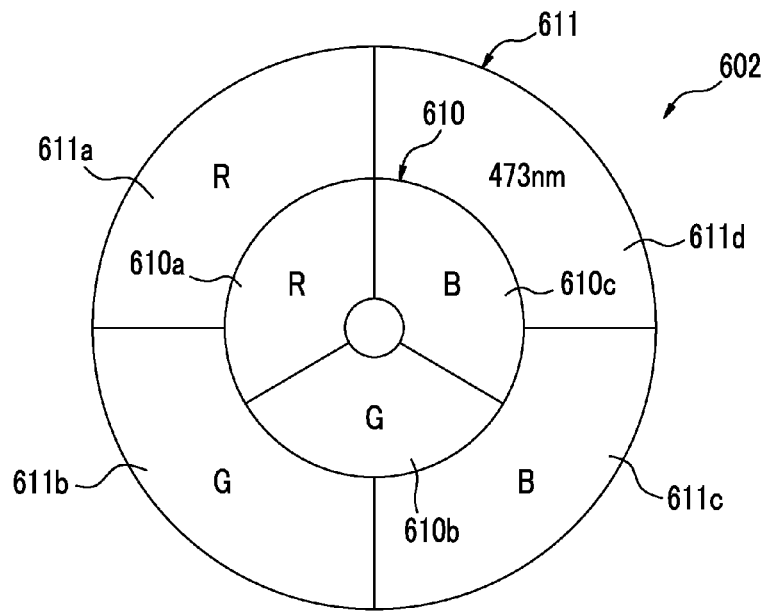
FIG. 25 is a plan view of a rotary filter.

As shown in FIG. 25, the normal observation mode filter 610 is provided in the inner peripheral portion of the rotary filter 602. The normal observation mode filter 610 includes an R filter 610a that transmits red light, a G filter 610b that transmits green light, and a B filter 610c that transmits blue light. Therefore, when the rotary filter 602 is placed at the first position for normal light observation mode, the white light from the broadband light source 601 is incident on one of the R filter 610a, the G filter 610b, and the B filter 610c according to the rotation of the rotary filter 602. As a result, red light, green light, and blue light are sequentially emitted to the observation target according to the transmitted filter, and the sensor 605 outputs sequentially an R image signal, a G image signal, and a B image signal by imaging the observation target with reflected light of the red light, the green light, and the blue light.

The special observation mode filter 611 is provided in the outer peripheral portion of the rotary filter 602. The special observation mode filter 611 includes an R filter 611a that transmits red light, a G filter 611b that transmits green light, a B filter 611c that transmits blue light, and a narrowband filter 611d that transmits narrowband light of 473±10 nm. Therefore, when the rotary filter 602 is placed at the second position for normal light observation mode, the white light from the broadband light source 601 is incident on one of the R filter 611a, the G filter 611b, the B filter 611c, and the narrowband filter 611d according to the rotation of the rotary filter 602. As a result, red light, green light, blue light, and narrowband light (473 nm) are sequentially emitted to the observation target according to the transmitted filter, and the sensor 605 outputs sequentially an R image signal, a G image signal, a B image signal, and a narrowband image signal by imaging the observation target with reflected light of the red light, the green light, the blue light, and the narrowband light.

The R image signal and the G image signal acquired in the special observation mode correspond to the R1 (or R2) image signal and the G1 (or G2) image signal in the first embodiment. In addition, the B image signal acquired in the special observation mode corresponds to the B2 image signal in the first embodiment, and the narrowband image signal corresponds to the B1 image signal. Accordingly, subsequent processing can be performed in approximately the same manner as in the endoscope system 10 according to the first embodiment.

However, in the endoscope system of this reference example, the oxygen saturation calculation section 83 calculates the oxygen saturation using three image signals of a narrowband image signal, an R image signal, and a G image signal. When it is determined that the movement of the observation target is small, the image generation section 84 generates an oxygen saturation image using the oxygen saturation and the image signals of R, and B. That is, when the movement of the observation target is small, it is possible to present the accurate oxygen saturation by using a total of four frames in order to calculate the oxygen saturation and generate an oxygen saturation image. This mode corresponds to the calculation of the oxygen saturation and the generation of an oxygen saturation image in the first mode of the first embodiment.

On the other hand, when it is determined that the movement of the observation target is large, the image generation section 84 generates an oxygen saturation image using the calculated oxygen saturation, narrowband image signal, R image signal, and G image signal. That is, when the movement of the observation target is large, only the image signals of a total of three frames are used in order to calculate the oxygen saturation and generate an oxygen saturation image. Therefore, it is possible to present the accurate oxygen saturation while suppressing a blur of the observation target in the oxygen saturation image or the like. This mode corresponds to the calculation of the oxygen saturation and the generation of an oxygen saturation image in the second mode of the first embodiment.

In addition, the broadband light source 601 and the rotary filter 602 form a light source that emits the first and second illumination light beams having different emission spectrums. In the present embodiment, a series of light emitted to the observation target by using the special observation mode filter 611 is the first illumination light, and a series of light emitted to the observation target by using the normal observation mode filter 610 is the second illumination light.

Although the oxygen saturation is calculated based on the signal ratio B1/G2 and the signal ratio R2/G2 or the signal ratio B1/G1 and the signal ratio R1/G1 in the first to fifth embodiments and the reference example, it is also possible to calculate the oxygen saturation based on only the signal ratio B1/G2 or the signal ratio B1/G1. In this case, it is preferable to store the correlation between the signal ratio B1/G2 or the signal ratio B1/G1 and the oxygen saturation in the correlation storage section 82.

Although the oxygen saturation image obtained by imaging the oxygen saturation is generated and displayed in the first to fifth embodiments and the reference example, a blood volume image obtained by imaging the blood volume may be generated and displayed in addition to the generation and display of the oxygen saturation image. Since the blood volume is correlated with the signal ratio R2/G2 (or R1/G1), it is possible to generate a blood volume image by imaging the blood volume by assigning different colors according to the signal ratio R2/G2 (or R1/G1).

In the first to fifth embodiments and the reference example, the oxygen saturation is calculated. However, instead of or in addition to the oxygen saturation, other biological function information, such as an oxygenated hemoglobin index that is calculated from "blood volume× oxygen saturation (%)" or a reduced hemoglobin index that is calculated from "blood volume×(1−oxygen saturation) (%)", may be calculated.

Figure 26:
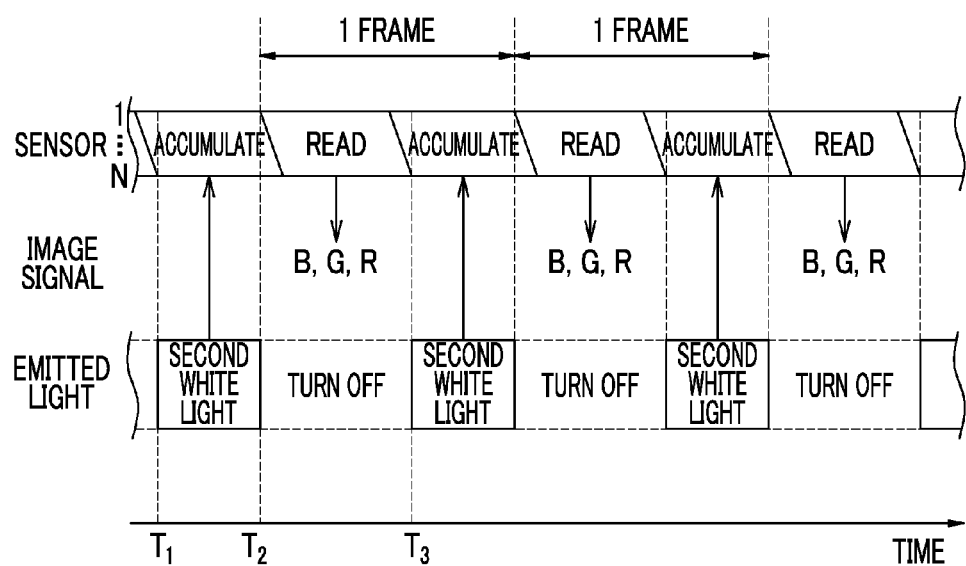
FIG. 26 is an explanatory view showing imaging control in the normal observation mode in the case of using a CMOS image sensor.
Figure 27:
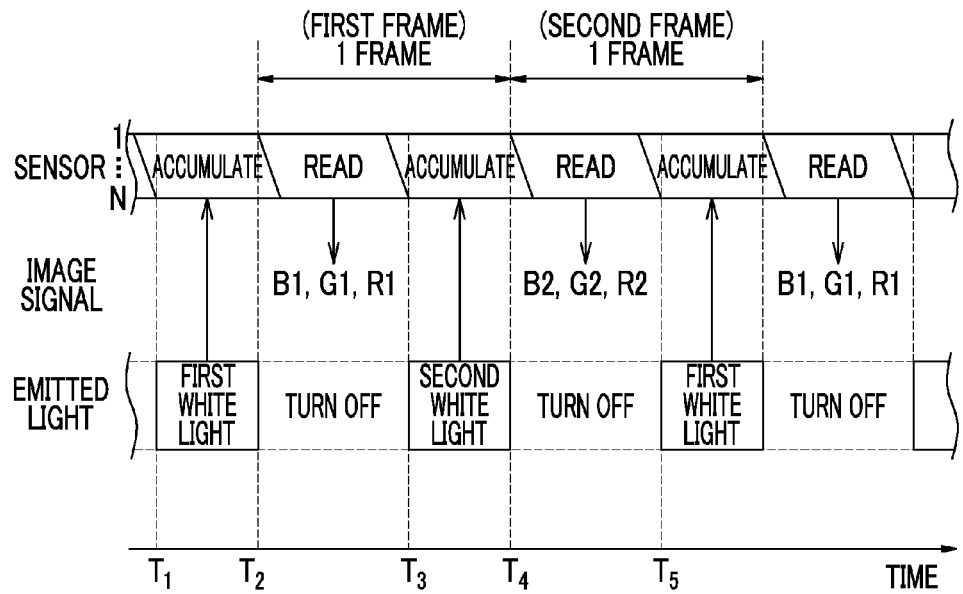
FIG. 27 is an explanatory view showing imaging control in the special observation mode in the case of using a CMOS image sensor.

Although the CCD image sensor is used as the sensor 48 in the first to fifth embodiments and the reference example, a CMOS image sensor may also be used as the sensor 48. In this case, the CMOS image sensor is driven in a so-called rolling shutter method, and accumulation and reading of the signal charge are sequentially performed for each row (each of first to N-th rows) of pixels. For this reason, the timing of the accumulation and reading of the signal charge of each row differs according to each row. Therefore, switching between the first white light and the second white light is preferably performed in accordance with the reading timing. For example as shown in FIG. 26, in the normal observation mode, the emission of the second white light is performed until the accumulation of the first row is completed (time $T_2$) from the start of the accumulation of the N-th row (time $T_1$), while the emission of the second white light is stopped until the reading of the N-th row is completed (time $T_3$) from the start of the reading of the first row (time $T_2$). In addition, as shown in FIG. 27, in the special observation mode, the emission of the second white light is performed until the accumulation of the first row is completed (time $T_2$) from the start of the accumulation of the N-th row (time $T_1$), while the emission of the second white light is stopped until the reading of the N-th row is completed (time $T_3$) from the start of the reading of the first row (time $T_2$). Then, in the next frame, the emission of the first white light is performed until the accumulation of the first row is completed (time $T_4$) from the start of the accumulation of the N-th row (time $T_3$), while the emission of the first white light is stopped until the reading of the N-th row is completed (time $T_5$) from the start of the reading of the first row (time $T_4$). Thus, it is possible to standardize the length (exposure) of the substantial charge accumulation period of each row and to prevent the signal based on the first white light and the signal based on the second white light from being mixed. Therefore, even when a CMOS image sensor is used as the sensor 48, it is possible to calculate an accurate oxygen saturation as in the embodiments described above. The same is true for a case when the LED light source unit 501 or the broadband light source 601 and the rotary filter 602 are used instead of the first and second blue laser light sources 34 and 36.

Figure 28:
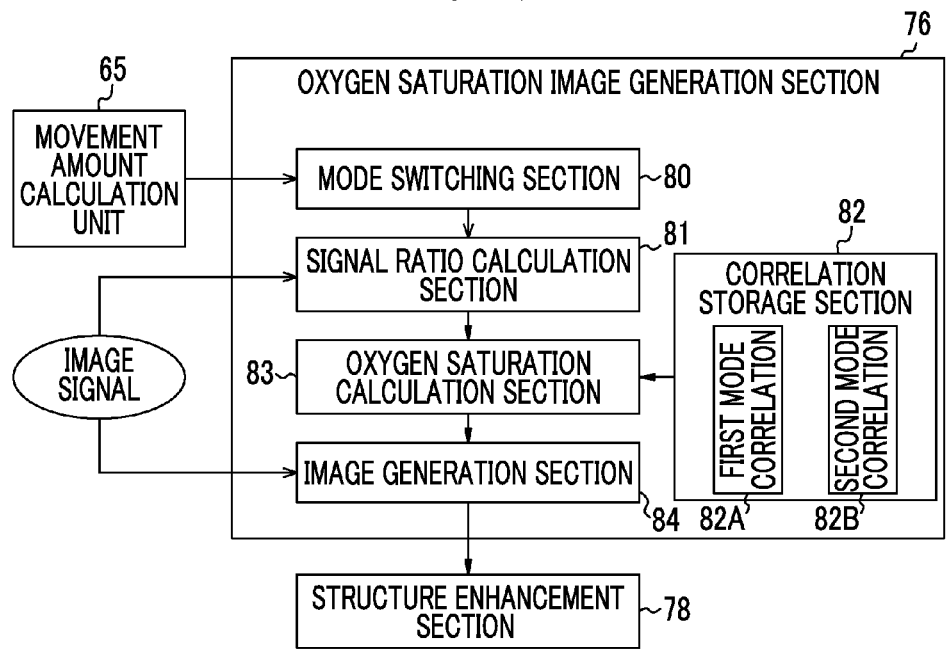
FIG. 28 is a block diagram of an oxygen saturation image generation section in which the correlation for first and second modes is stored.

In the first to fifth embodiments and the reference example, the correlation stored in the correlation storage section 82 is used commonly in the first and second modes. However, as shown in FIG. 28, a first mode correlation 82A and a second mode correlation 82B may be stored in the correlation storage section 82, and the corresponding correlation may be used in each calculation mode.

What is claimed is:

1. An endoscope system, comprising:
a light source that emits first illumination light and second illumination light having different emission spectrums;
an imaging device that images an observation target under illumination with the first illumination light and outputs a first image signal and images the observation target under illumination with the second illumination light and outputs a second image signal;
a movement amount calculation unit that calculates a movement amount of the observation target based on the first or second image signal; and
an oxygen saturation calculation unit that calculates an oxygen saturation in a first mode of using the first and second image signals in a case where the movement amount is within a specific range, and calculates an oxygen saturation in a second mode of using the first image signal in a case where the movement amount is larger than the specific range.

2. The endoscope system according to claim 1,
wherein the movement amount calculation unit calculates one movement amount in an entire imaging region expressed by the first or second image signal, and
the first and second modes are changed at once in the entire imaging region.

3. The endoscope system according to claim 1,
wherein the movement amount calculation unit divides an imaging region expressed by the first or second image signal into a plurality of regions and calculates the movement amount for each of the regions, and
the oxygen saturation calculation unit calculates the oxygen saturation in the first mode for the region where the movement amount falls within a specific range set in advance, and calculates the oxygen saturation in the second mode for the region where the movement amount does not fall within the specific range.

4. The endoscope system according to claim 3, wherein the movement amount calculation unit calculates the movement amount for each pixel of the first or second image signal.

5. The endoscope system according to claim 1, further comprising:
a light source control unit that performs control to emit the first illumination light and the second illumination light alternately in both of the first and second modes by controlling light emission timings of the first illumination light and the second illumination light.

6. The endoscope system according to claim 2, further comprising:
a light source control unit that performs control to emit the first illumination light and the second illumination light alternately in both of the first and second modes by controlling light emission timings of the first illumination light and the second illumination light.

7. The endoscope system according to claim 3, further comprising:
a light source control unit that performs control to emit the first illumination light and the second illumination light alternately in both of the first and second modes by controlling light emission timings of the first illumination light and the second illumination light.

8. The endoscope system according to claim 1, further comprising:
a light source control unit that performs control to emit the first illumination light and the second illumination light alternately in the first mode and emit only the first illumination light in the second mode by controlling light emission timings of the first illumination light and the second illumination light.

9. The endoscope system according to claim 2, further comprising:
a light source control unit that performs control to emit the first illumination light and the second illumination light alternately in the first mode and emit only the first illumination light in the second mode by controlling light emission timings of the first illumination light and the second illumination light.

10. The endoscope system according to claim 3, further comprising:
a light source control unit that performs control to emit the first illumination light and the second illumination light alternately in the first mode and emit only the first illumination light in the second mode by controlling light emission timings of the first illumination light and the second illumination light.

11. The endoscope system according to claim 1, wherein the movement amount calculation unit calculates the movement amount based on a ratio between a red image signal included in the first image signal and a red image signal included in the second image signal.

12. The endoscope system according to claim 2, wherein the movement amount calculation unit calculates the movement amount based on a ratio between a red image signal included in the first image signal and a red image signal included in the second image signal.

13. The endoscope system according to claim 1, wherein the first mode is a calculation mode in which the oxygen saturation is calculated based on a ratio between a blue image signal included in the first image signal and a green image signal included in the second image signal, and
the second mode is a calculation mode in which the oxygen saturation is calculated based on a ratio between blue and green image signals included in the first image signal.

14. An endoscope system, comprising:
a light source that emits first illumination light and second illumination light having different emission spectrums;
an imaging device that images an observation target under illumination with the first illumination light and outputs a first image signal and images the observation target under illumination with the second illumination light and outputs a second image signal;
a movement amount calculation unit that calculates a movement amount of the observation target based on the first or second image signal;
an oxygen saturation calculation unit that calculates an oxygen saturation in a first mode of using the first and second image signals, and calculate an oxygen saturation in a second mode of using the first image signal; and
further the oxygen saturation calculation unit includes a first mode image generation unit that generates a first mode image as an oxygen saturation image showing an oxygen saturation calculated in the first mode, a second mode image generation unit that generates a second mode image as an oxygen saturation image showing an oxygen saturation calculated in the second mode, and a weighting combination unit that generates a weighting ratio of the second mode image to the first mode image, which is larger as the movement amount is larger, and further the weighting combination unit composites the weighted first and second mode images corresponding to the weighting ratio to generate a composite oxygen saturation image.

15. A processor device for an endoscope system including a light source that emits first illumination light and second illumination light having different emission spectrums and an imaging device that images an observation target under illumination with the first illumination light and outputs a first image signal and images the observation target under illumination with the second illumination light and outputs a second image signal, the processor device for an endoscope system comprising:
a reception unit that receives the first and second image signals;
a movement amount calculation unit that calculates a movement amount of the observation target based on the first or second image signal; and
an oxygen saturation calculation unit that calculates an oxygen saturation in a first mode of using the first and second image signals in a case where the movement amount is within a specific range and calculates an oxygen saturation in a second mode of using the first image signal in a case where the movement amount is larger than the specific range.

16. An operation method for the endoscope system according to claim 1, comprising:
a step of emitting first illumination light and second illumination light having different emission spectrums using a light source and imaging an observation target under illumination with the first illumination light and outputting a first image signal and imaging the observation target under illumination with the second illumination light and outputting a second image signal using an imaging device;

a step of calculating a movement amount of the observation target based on the first or second image signal using a movement amount calculation unit; and a step of calculating an oxygen saturation in a first mode of using the first and second image signals in a case where the movement amount is within a specific range and calculates an oxygen saturation in a second mode of using the first image signal in a case where the movement amount is larger than the specific range.

17. An operation method for a processor device used in an endoscope system including a light source that emits first illumination light and second illumination light having different emission spectrums and an imaging device that images an observation target under illumination with the first illumination light and outputs a first image signal and images the observation target under illumination with the second illumination light and outputs a second image signal, the operation method for a processor device comprising:

a step of receiving the first and second image signals using a reception unit;

a step of calculating a movement amount of the observation target based on the first or second image signal using a movement amount calculation unit; and a step of calculating an oxygen saturation in a first mode of using the first and second image signals in a case where the movement amount is within a specific range and calculates an oxygen saturation in a second mode of using the first image signal in a case where the movement amount is larger than the specific range.

* * * * *